(12) United States Patent
Gérard et al.

(10) Patent No.: US 10,385,071 B2
(45) Date of Patent: Aug. 20, 2019

(54) METHODS OF PREPARING CYTOTOXIC BENZODIAZEPINE DERIVATIVES

(71) Applicant: IMMUNOGEN, INC., Waltham, MA (US)

(72) Inventors: Baudouin Gérard, Belmont, MA (US); Richard A. Silva, Needham, MA (US); Michael Louis Miller, Framingham, MA (US); Manami Shizuka, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/878,991

(22) Filed: Jan. 24, 2018

(65) Prior Publication Data

US 2018/0251474 A1    Sep. 6, 2018

Related U.S. Application Data

(60) Provisional application No. 62/450,270, filed on Jan. 25, 2017.

(51) Int. Cl.
*C07D 487/04* (2006.01)
*C07D 519/00* (2006.01)
*C07C 205/19* (2006.01)
*C07D 207/452* (2006.01)
*C07D 519/04* (2006.01)

(52) U.S. Cl.
CPC .......... *C07D 519/00* (2013.01); *C07C 205/19* (2013.01); *C07D 207/452* (2013.01); *C07D 487/04* (2013.01); *C07D 519/04* (2013.01)

(58) Field of Classification Search
CPC .......................... C07D 487/04; C07D 519/00
See application file for complete search history.

(56) References Cited

U.S. PATENT DOCUMENTS 10,081,640 B2 * 9/2018 Gerard ................. C07D 519/00

FOREIGN PATENT DOCUMENTS

| WO | 2012/128868 A1 | 9/2012 |
| WO | 2017/004026 A1 | 1/2017 |
| WO | 2017/015496 A1 | 1/2017 |

* cited by examiner

*Primary Examiner* — Bruck Kifle
(74) *Attorney, Agent, or Firm* — McCarter & English, LLP; Stephen G. Davis; Xin Zhang

(57) ABSTRACT

The invention provides novel methods for preparing indolinobenzodiazepine dimer compounds and their synthetic precursors.

19 Claims, 3 Drawing Sheets

METHODS OF PREPARING CYTOTOXIC BENZODIAZEPINE DERIVATIVES

RELATED APPLICATION

This application claims the benefit of the filing date, under 35 U.S.C. § 119(e), of U.S. Provisional Application No. 62/450,270, filed on Jan. 25, 2017, the entire contents of which are incorporated herein by reference.

FIELD OF THE INVENTION

The present invention relates to novel methods for preparing cytotoxic indolinobenzodiazepine derivatives.

BACKGROUND OF THE INVENTION

It has been shown that cell-binding agent conjugates of indolinobenzodiazepine dimers that have one imine functionality and one amine functionality display a much higher therapeutic index (ratio of maximum tolerated dose to minimum effective dose) in vivo compared to previously disclosed benzodiazepine derivatives having two imine functionalities. See, for example, WO 2012/128868. The previously disclosed method for making the indolinobenzodiazepine dimers with one imine functionality and one amine functionality involves partial reduction of indolinobenzodiazepine dimers having two imine functionalities. The partial reduction step generally leads to the formation of fully reduced by-product and unreacted starting material, which requires cumbersome purification step and results in low yield.

Thus, there exists a need for improved methods for preparing the indolinobenzodiazepine dimers that are more efficient and suitable for large scale manufacturing process.

SUMMARY OF THE INVENTION

The present invention provides modular synthetic methods for preparing indolinobenzodiazepine dimer compounds and their synthetic precursors. Compared to the previously disclosed methods, the methods of the present invention are modular and more versatile as well as suitable for large scale manufacturing process.

In one embodiment, the present invention provides a method of preparing a compound of formula (A):

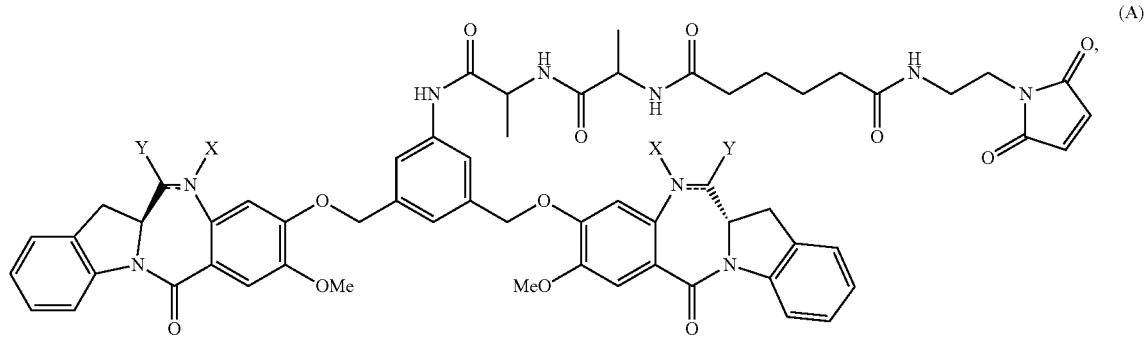

or a salt thereof, comprising reacting a compound of formula (V):

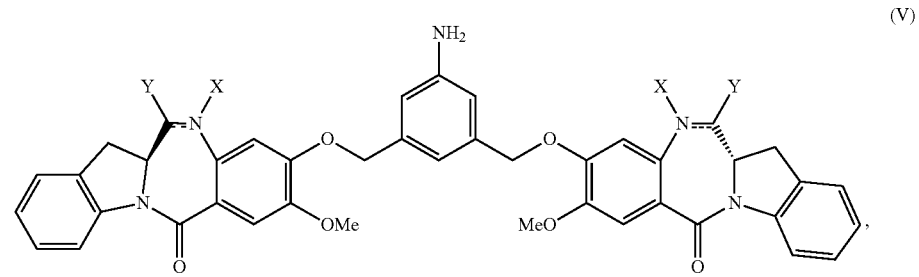

or a salt thereof, with a compound of formula (X):

wherein:

each double line == between N and C independently represents a single bond or a double bond, provided that when it is a double bond X is absent and Y is —H, and when it is a single bond, X and Y are both —H; and E is —OH, halide or —C(=O)E is an activated ester.

In another embodiment, the present invention provides a method of preparing a compound of formula (A):

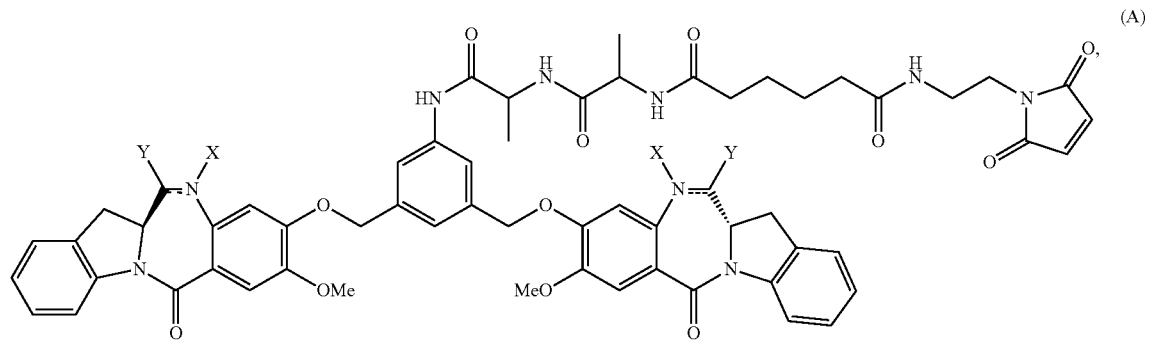

or a salt thereof, comprising the steps of:
1) reacting a compound of formula (IV):

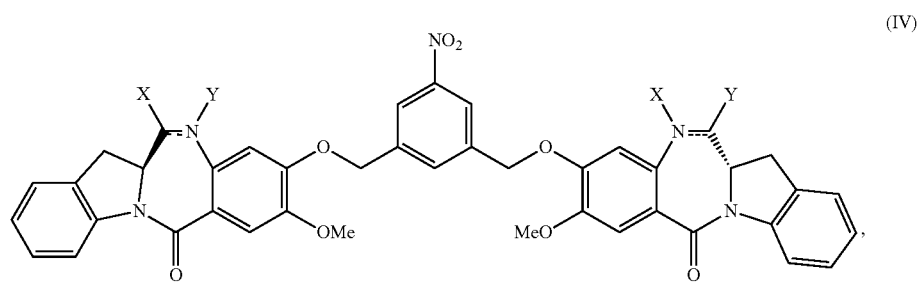

or a salt thereof, with a reducing agent to form a compound of formula (V):

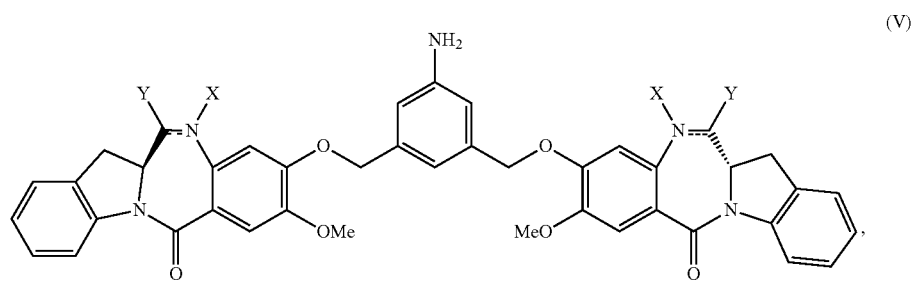

or a salt thereof; and 2) reacting the compound of formula (V) or a salt thereof, with a compound of formula (X):

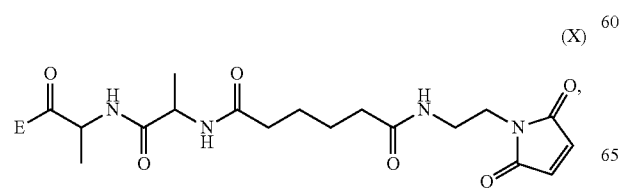

wherein:

each double line == between N and C independently represents a single bond or a double bond, provided that when it is a double bond X is absent and Y is —H, and when it is a single bond, X and Y are both —H; and E is —OH, halide or —C(=O)E is an activated ester.

Also provided in the present invention is a method of preparing a compound of formula (Xa):

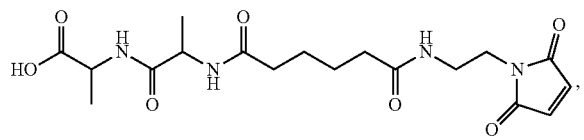

or a salt thereof, comprising reacting the compound of formula (IX):

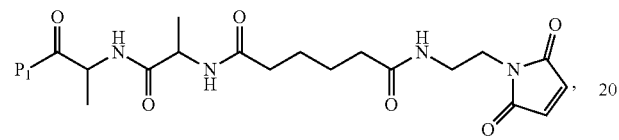

or a salt thereof, with a carboxylic acid deprotecting agent, wherein $P_1$ is a carboxylic acid protecting group.

In another embodiment, the present invention is directed to a method of preparing a compound of formula (IX):

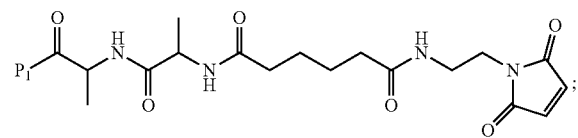

comprising reacting a compound of formula (VIII):

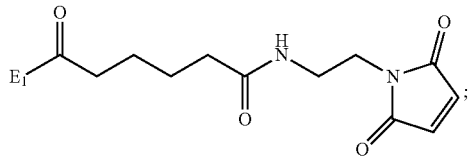

or a salt thereof, with a compound of formula (c):

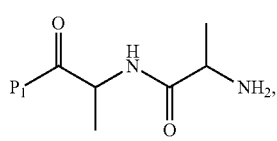

or a salt thereof, wherein $E_1$ is —OH, halide or —C(=O)$E_1$ is an activated ester; and $P_1$ is a carboxylic acid protecting group.

In yet another embodiment, the present invention provides a method of preparing a compound of formula (Xa):

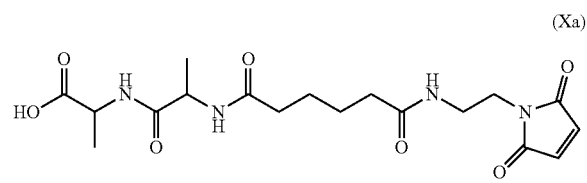 [SMILES: CC(NC(=O)C(C)NC(=O)CCCCC(=O)NCCN1C(=O)C=CC1=O)C(=O)O]

or a salt thereof, comprising the steps of:

1) reacting a compound of formula (VIII):

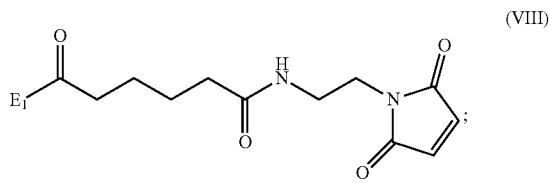

or a salt thereof, with a compound of formula (c):

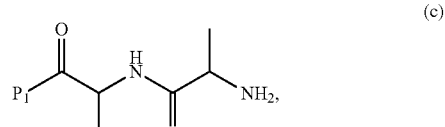

or a salt thereof, to form a compound of formula (IX):

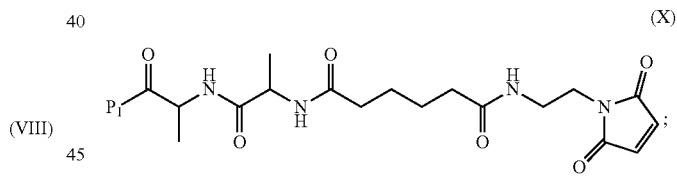

and 2) reacting the compound of formula (IX) with a carboxylic acid deprotecting agent, wherein $E_1$ is —OH, halide or —C(=O)$E_1$ is an activated ester; and $P_1$ is a carboxylic acid protecting group.

Also provided in the present invention is a method of preparing a compound of formula (II),

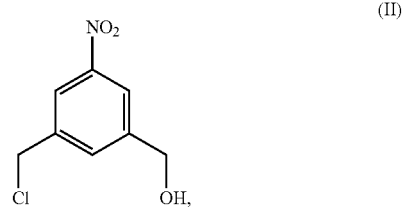 [SMILES: O=[N+]([O-])c1cc(CO)cc(CCl)c1]

comprising reacting a compound of formula (I):

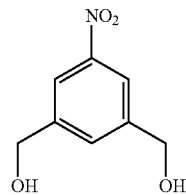
(I)

with hydrochloric acid in toluene.

In another embodiment, the present invention is directed to a method of preparing a compound of formula (IV):

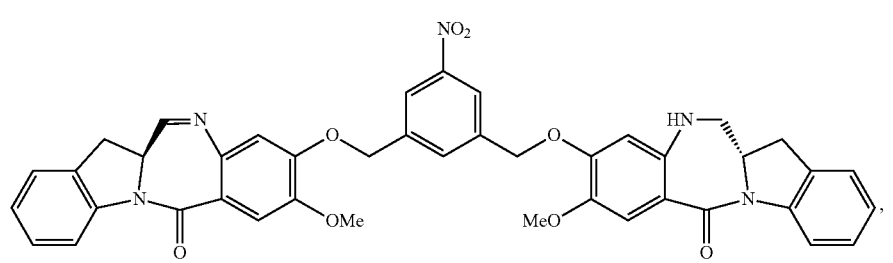
(IV)

or a salt thereof, comprising the steps of:

1) reacting a compound of formula (I):

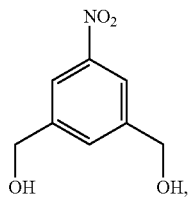
(I)

with hydrochloric acid in toluene to form a compound of formula (II):

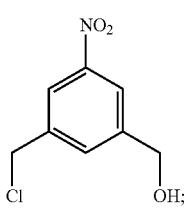
(II)

2) reacting the compound of formula (II) with a monomer compound of formula (a),

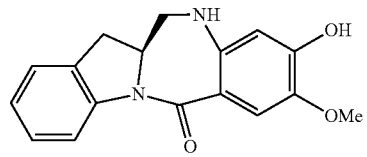
(a)

to form a compound of formula (III):

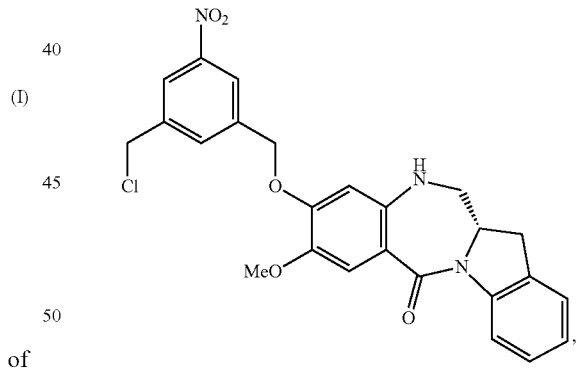
(III)

or a salt thereof;

3) reacting the compound of formula (III) or a salt thereof with a monomer compound of formula (b):

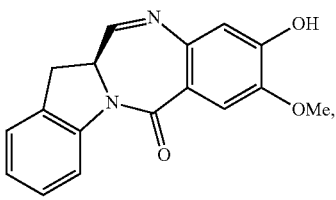
(b)

to form the compound of formula (IV) or a salt thereof.

In another embodiment, the present invention provides a method of preparing a compound of formula (A-1):

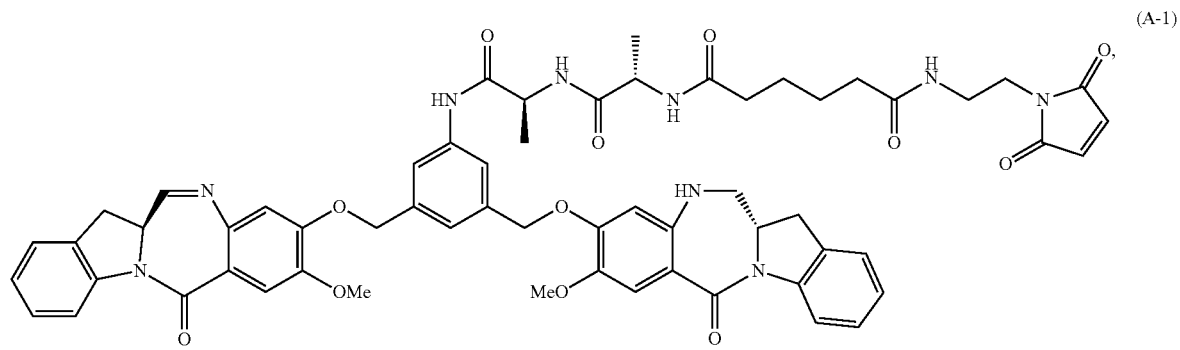 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

or a salt thereof, comprising the steps of:
1) reacting a compound of formula (I):

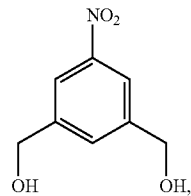

with hydrochloric acid in toluene to form a compound of formula (II):

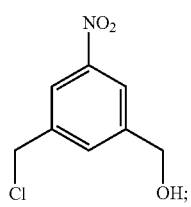

2) reacting the compound of formula (II) with a monomer compound of formula (a),

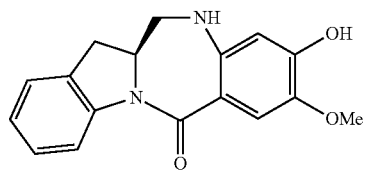

to form a compound of formula (III):

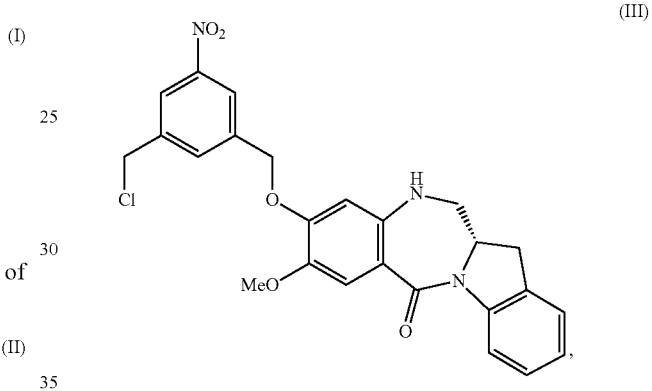

or a salt thereof;

3) reacting the compound of formula (III) or a salt thereof with a monomer compound of formula (b):

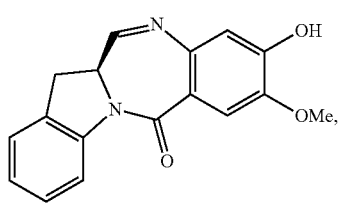

to form a compound of formula (IV-1):

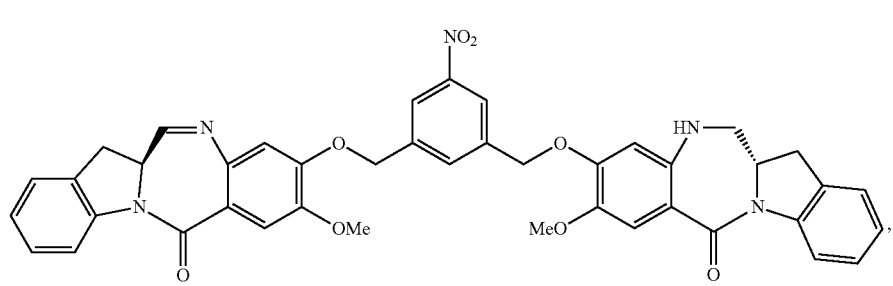

or a salt thereof;

4) reacting the compound of formula (IV) or a salt thereof with a reducing agent to form a compound of formula (V-1):

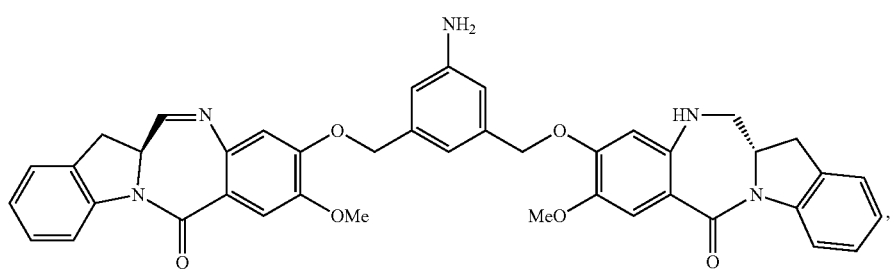

(V-1)

or a salt thereof; and 5) reacting the compound of formula (V-1) or a salt thereof, with a compound of formula (X-1):

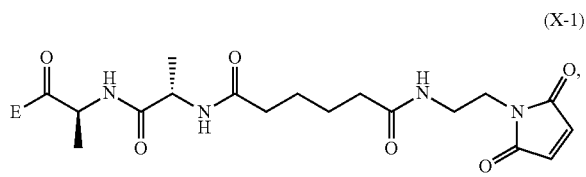

(X-1)

to form the compound of formula (A-1) or a salt thereof, wherein E is —OH, halide or —C(=O)E is an activated ester.

The present invention also provide compounds described herein, such as compounds of formula (VII), (VIII), (VIIIa), (IX), (IX-1), (X), (Xa), (X-1) or (X-1a) or a salt thereof.

DETAILED DESCRIPTION OF THE INVENTION

Figure 1:
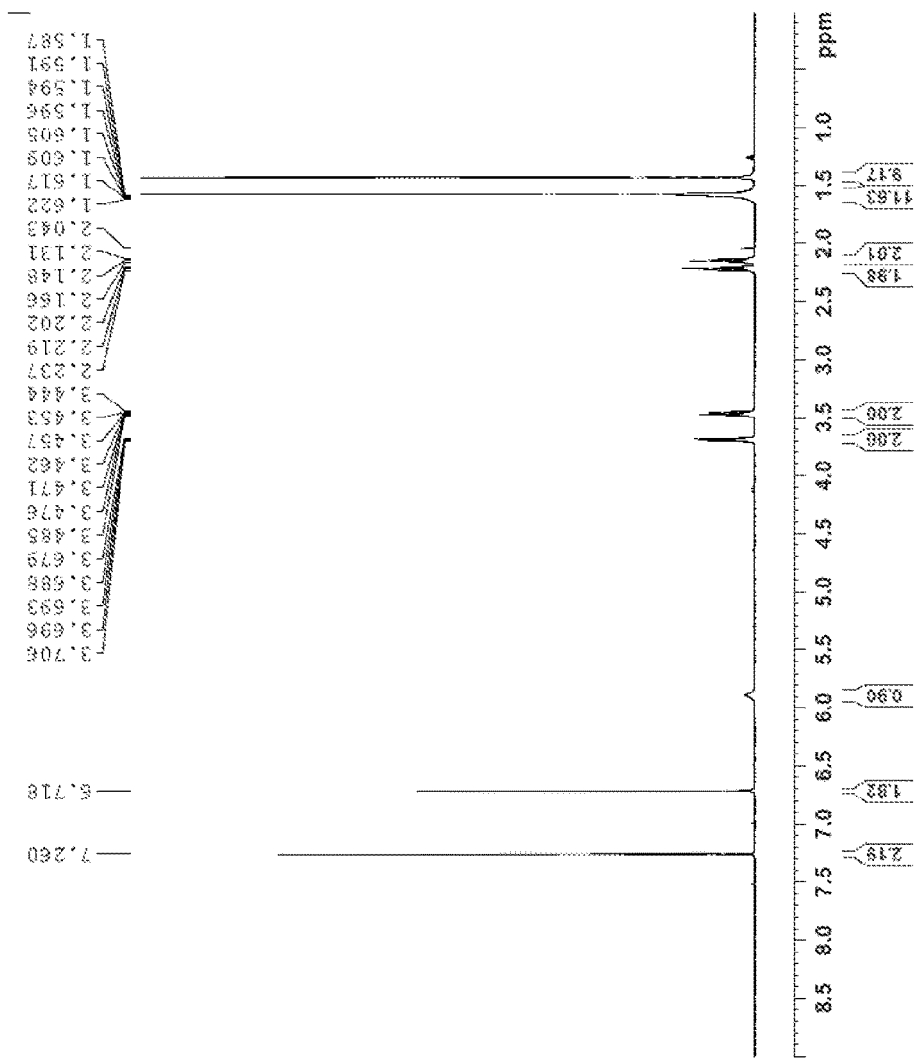
FIGS. 1-3 show proton NMR spectra of the compounds of the present invention.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

Definitions

"Alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alky group or $C_3$-$C_6$ for branched chain alkyl). Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or $C_{x\text{-}xx}$alky means a linear or branched alkyl having x-xx carbon atoms.

The term "aryl" as used herein, include substituted or unsubstituted single-ring aromatic groups in which each atom of the ring is carbon. Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl (benzene), tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

The term "heteroaryl" as used herein, refers to substituted or unsubstituted aromatic single ring structures, preferably 5- to 7-membered rings, more preferably 5- to 6-membered rings, whose ring structures include at least one heteroatom (e.g., 0, N, or S), preferably one to four or one to three heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more ring atoms are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaromatics, and/or heterocyclyls. In some preferred embodiments, polycyclic heteroaryls have 2-3 rings. In certain embodiments, preferred polycyclic heteroaryls have two cyclic rings in which both of the rings are aromatic. In certain embodiments, each ring of the polycycle contains from 3 to 10 atoms in the ring, preferably from 5 to 7 atoms in the ring. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The heteroaryl groups can be carbon (carbon-linked) or nitrogen (nitrogen-linked) attached where such is possible. By way of example and not limitation, carbon bonded heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, thiofuran, thiophene, or pyrrole, position 2, 4, or 5 of an oxazole, imidazole or thiazole, position 3, 4, or 5 of an isoxazole, pyrazole, or isothiazole, position 2, 3, 4, 5, 6, 7, or 8 of a quinoline or position 1, 3, 4, 5, 6, 7, or 8 of an isoquinoline.

By way of example and not limitation, nitrogen bonded heteroaryls are bonded at position 1 of a pyrrole, imidazole, pyrazole, indole, 1H-indazole, position 2 of a isoindole, and position 9 of a carbazole, or β-carboline.

The heteroatoms present in heteroaryl include the oxidized forms such as NO, SO, and $SO_2$.

As used herein, an "activated ester" refers to an ester group that is readily displaced by a hydroxyl or an amine group. Exemplary activated esters include, but are not limited to N-hydroxysuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, pentafluorophenyl ester, nitropyridyl (e.g., 4-nitropyridyl) ester, trifluoroacetate, and acetate.

The term "halide" refers to F, Cl, Br or I. In one embodiment, the halide is Cl. In one embodiment, the halide is Br. In one embodiment, the halide is I. In one embodiment, the halide is F.

The term "compound" is intended to include compounds for which a structure or formula or any derivative thereof has been disclosed in the present invention or a structure or formula or any derivative thereof that has been incorporated by reference. The term also includes, stereoisomers, geometric isomers, or tautomers. The specific recitation of "stereoisomers," "geometric isomers," "tautomers," "salt" in certain aspects of the invention described in this application shall not be interpreted as an intended omission of these forms in other aspects of the invention where the term "compound" is used without recitation of these other forms.

The term "precursor" of a given group refers to any group which may lead to that group by any deprotection, a chemical modification, or a coupling reaction.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "protecting group" or "protecting moiety" refers to a substituent that is commonly employed to block or protect a particular functionality while reacting other functional groups on the compound, a derivative thereof, or a conjugate thereof.

An "carboxylic acid protecting group" is a substituent attached to an carbonyl group that blocks or protects the carboxylic acid functionality in the compound. Such groups are well known in the art (see for example, P. Wuts and T. Greene, 2007, Protective Groups in Organic Synthesis, Chapter 5, J. Wiley & Sons, NJ). Suitable carboxylic acid protecting group include, but are not limited to, alkyl ester (e.g., methyl ester or tert-butyl ester), benzyl ester, thioester (e.g., tert-butyl thioester), silyl ester (e.g., trimethylsilyl ester), 9-fluorenylmehtyl ester, (2-trimethylsilyl)ethoxymethyl ester, 2-(trimethylsilyl)ethyl ester, diphenylmethyl ester or oxazoline. In certain embodiments, the carboxylic acid protecting group is methyl ester, tert-butyl ester, benzyl ester or trimethylsilyl ester. In certain embodiments, the carboxylic acid protecting group is tert-butyl ester.

As used herein, "carboxylic acid deprotecting agent" refers a reagent that is capable of cleaving a carboxylic acid protecting group to form free carboxylic acid. Such reagents are well known in the art (see for example P. Wuts and T. Greene, 2007, Protective Groups in Organic Synthesis, Chapter 5, J. Wiley & Sons, NJ) and depend on the carboxylic acid protecting group used. For example, when the carboxylic acid protecting group is tert-butyl ester, it can be cleaved with an acid. In certain embodiment, the carboxylic acid deprotecting agent is trifluoroacetic acid.

As used herein, "alcohol activating agent" refers a reagent that increases the reactivity of a hydroxyl group thereby making the hydroxyl group a better leaving group. Examples of such alcohol activating agents include p-toluenesulfonyl chloride, thionyl chloride, triflic anhydride, mesyl chloride, mesyl anhydride, triphenylphosphine, acyl chloride, 4-dimethylaminopyridine, and others. In certain embodiments, the alcohol activating agent is thionyl chloride. In certain embodiment, the alcohol activating agent is triphenylphosphine.

The phrase "salt" as used herein, refers to an organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A salt may involve the inclusion of another molecule such as an acetate ion, a succinate ion or other counter ion. The counter ion may be any organic or inorganic moiety that stabilizes the charge on the parent compound. Furthermore, a salt may have more than one charged atom in its structure. Instances where multiple charged atoms are part of the salt can have multiple counter ions. Hence, a salt can have one or more charged atoms and/or one or more counter ion.

If the compound of the invention is a base, the desired salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

Methods of the Present Invention

The present invention provides modular synthetic methods for preparing indolinobenzodiazepine dimer compounds and precursors. The precursor compounds prepared by the present invention, such as the compound of formula (V) or (V-1) or a salt thereof described below, can be used for synthesizing indolinobenzodiazepine dimer compounds having diverse linkers for covalent linkage with cell-binding agents to form cell-binding agent-indolinobenzodiazepine conjugates.

In a first embodiment, the present invention provides a method of preparing a compound of formula (A):

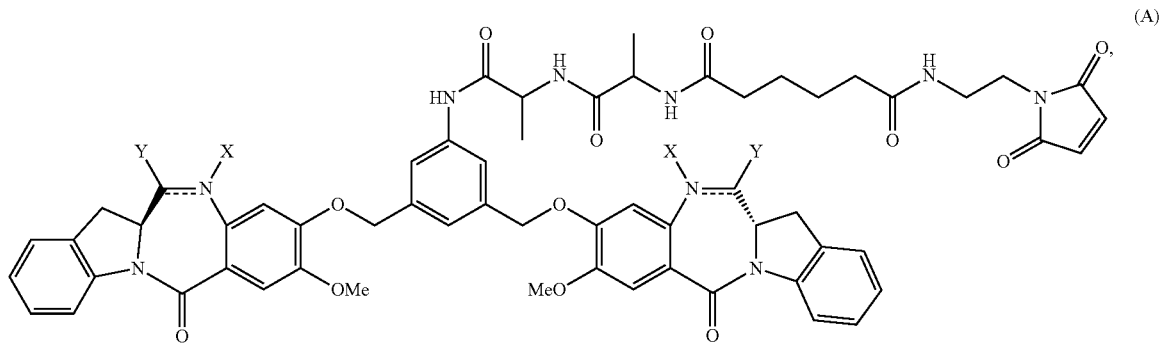

(A)

or a salt thereof, comprising reacting a compound of formula (V):

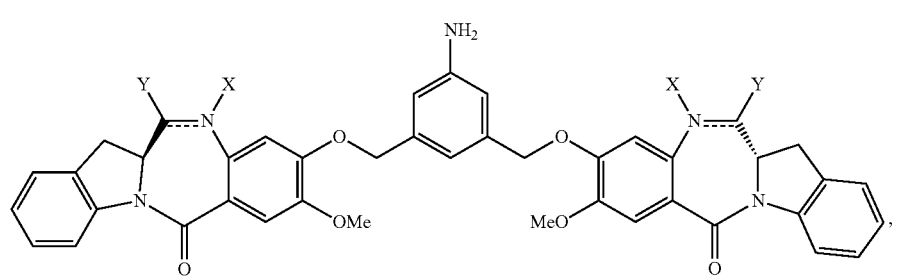

or a salt thereof, with a compound of formula (X):

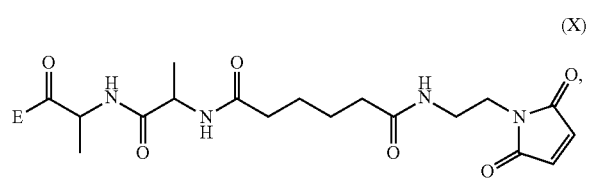

wherein:

each double line $=\!=$ between N and C independently represents a single bond or a double bond, provided that when it is a double bond X is absent and Y is —H, and when it is a single bond, X and Y are both —H; and E is —OH, halide or —C(=O)E is an activated ester.

Also included in the first embodiment is a method a method of preparing a compound of formula (dA):

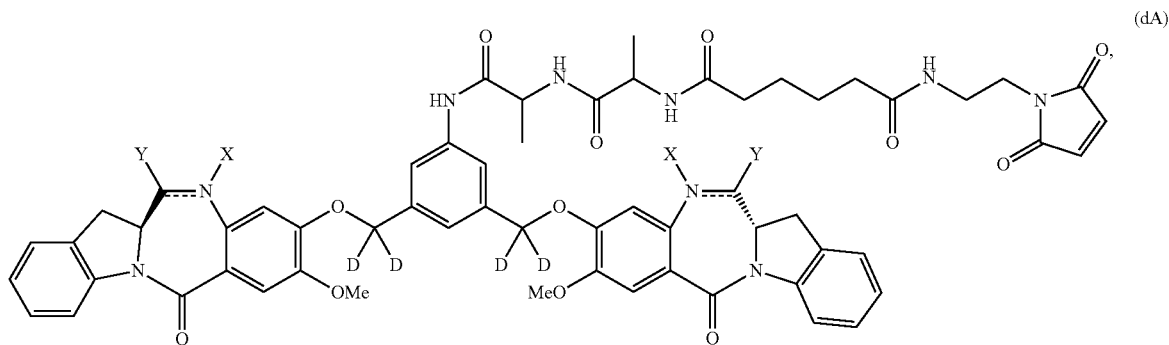

or a salt thereof, comprising reacting a compound of formula (dV):

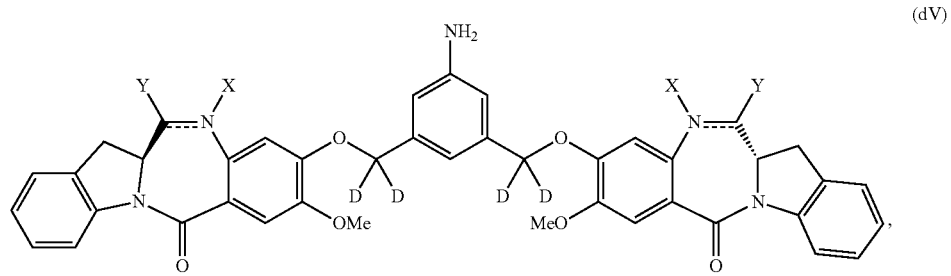

or a salt thereof, with a compound of formula (X):

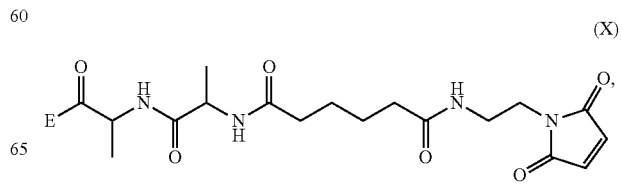

wherein the variables are the same as described for formula (A).

In certain embodiments, for compounds of formula (A) or (dA), both double line == between N and C independently represent a double bond. In certain embodiments, both double line == between N and C independently represent a single bond.

In certain embodiments, for compounds of formula (A) or (dA), one of the double line == between N and C represents a double bond; and the other double line == between N and C represents a single bond, the compound of formula (A) is represented by the following formula:

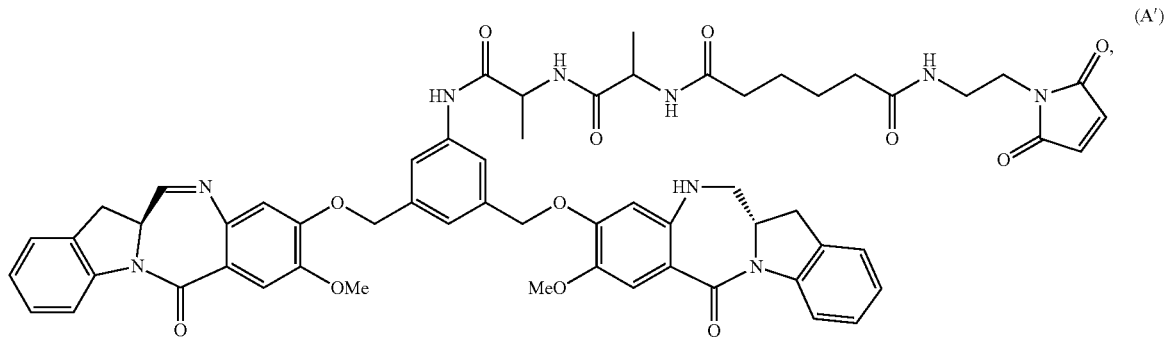 [SMILES: COc1cc2c(cc1OCc1cc(COc3cc4c(cc3OC)C(=O)N3c5ccccc5C[C@H]3CN4)cc(NC(=O)C(C)NC(=O)C(C)NC(=O)CCCCC(=O)NCCN3C(=O)C=CC3=O)c1)N=C[C@@H]1Cc3ccccc3N1C2=O]
(A')

or a salt thereof, and the compound of formula (dA) is represented by the following formula:

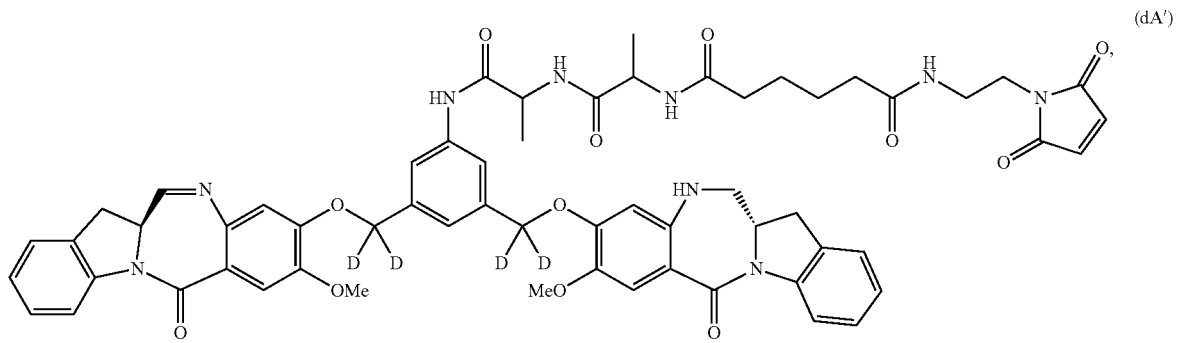 [SMILES: [2H]C([2H])(Oc1cc2c(cc1OC)C(=O)N1c3ccccc3C[C@H]1C=N2)c1cc(NC(=O)C(C)NC(=O)C(C)NC(=O)CCCCC(=O)NCCN2C(=O)C=CC2=O)cc(C([2H])([2H])Oc2cc3c(cc2OC)C(=O)N2c4ccccc4C[C@H]2CN3)c1]
(dA')

or a salt thereof.

In a second embodiment, for method described in the first embodiment, the compound of formula (A) or a salt thereof is represented by formula (A-1):

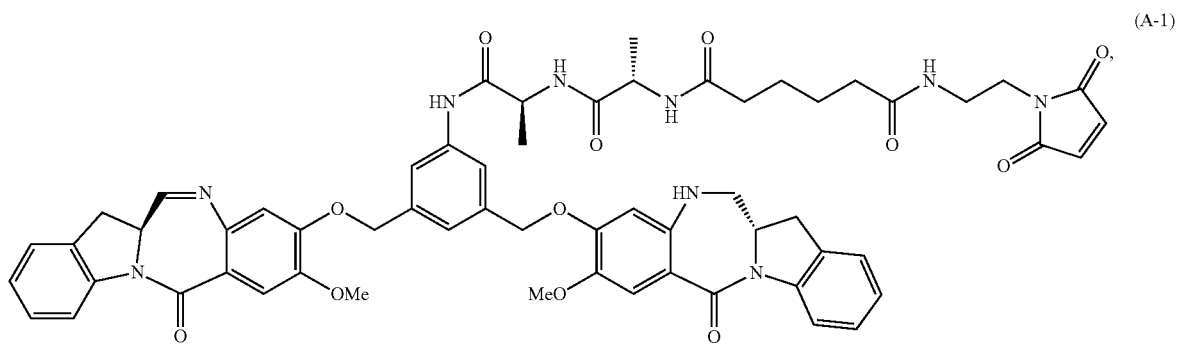 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]
(A-1)

or a salt thereof, and the method comprises reacting a compound of formula (V-1):

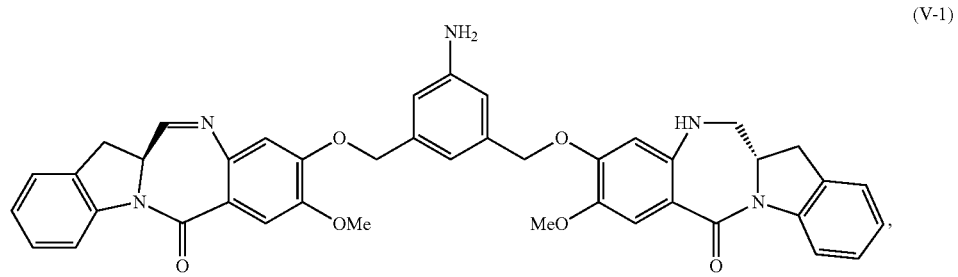 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

or a salt thereof, with a compound of formula (X-1):

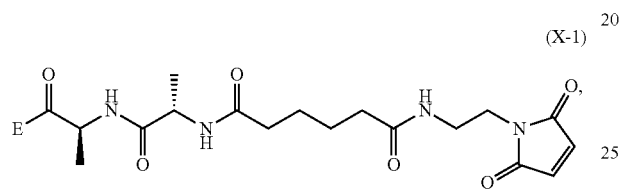

wherein E is —OH, halide or —C(=O)E is an activated ester.

Also in the second embodiment, for method described in the first embodiment, the compound of formula (dA) or a salt thereof is represented by formula (dA-1):

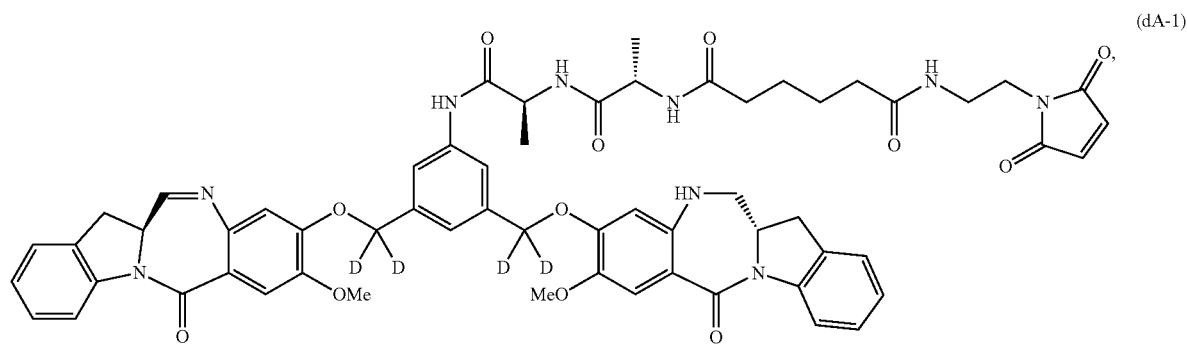 [SMILES: [2H]C([2H])(Oc1cc2c(cc1OC)C(=O)N1c3ccccc3C[C@H]1C=N2)c1cc(NC(=O)[C@H](C)NC(=O)[C@H](C)NC(=O)CCCCC(=O)NCCN2C(=O)C=CC2=O)cc(C([2H])([2H])Oc2cc3c(cc2OC)C(=O)N2c4ccccc4C[C@H]2CN3)c1]

or a salt thereof, and the method comprises reacting a compound of formula (dV-1):

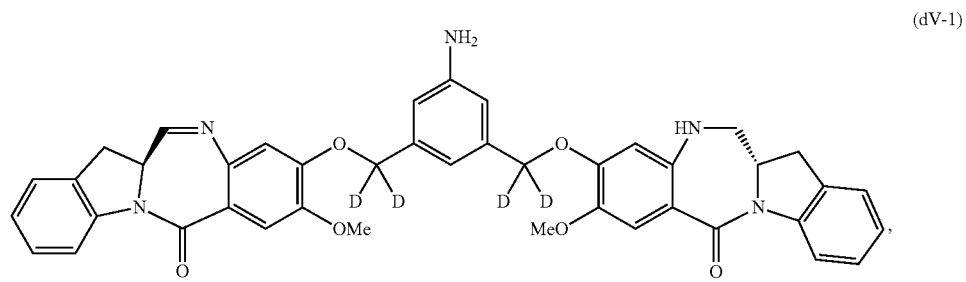 [SMILES: [2H]C([2H])(Oc1cc2c(cc1OC)C(=O)N1c3ccccc3C[C@H]1C=N2)c1cc(N)cc(C([2H])([2H])Oc2cc3c(cc2OC)C(=O)N2c4ccccc4C[C@H]2CN3)c1]

or a salt thereof, with a compound of formula (X-1):
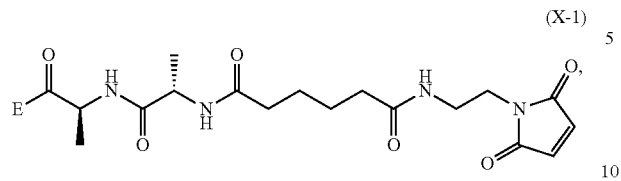
wherein E is —OH, halide or —C(=O)E is an activated ester.
In a third embodiment, the present invention provides a method of preparing a compound of formula (A):
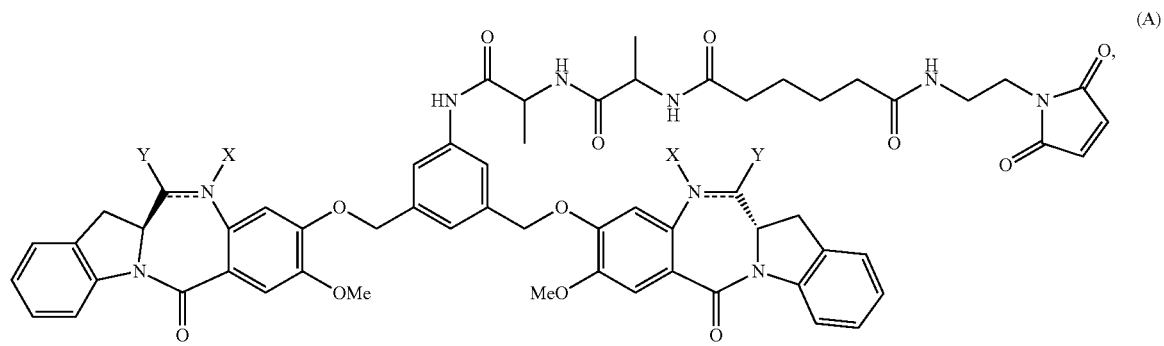
or a salt thereof, comprising the steps of:
1) reacting a compound of formula (IV):
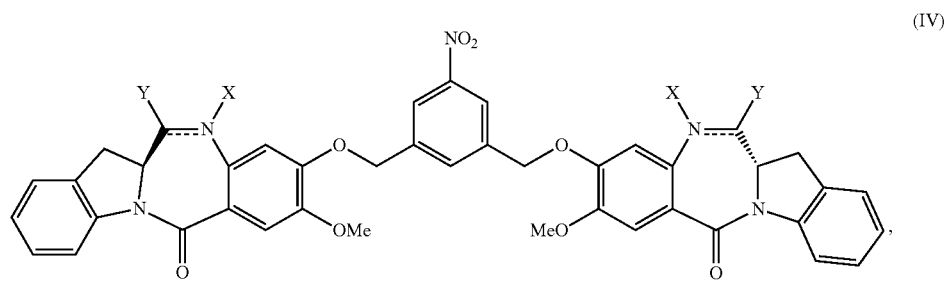
or a salt thereof, with a reducing agent to form a compound of formula (V):
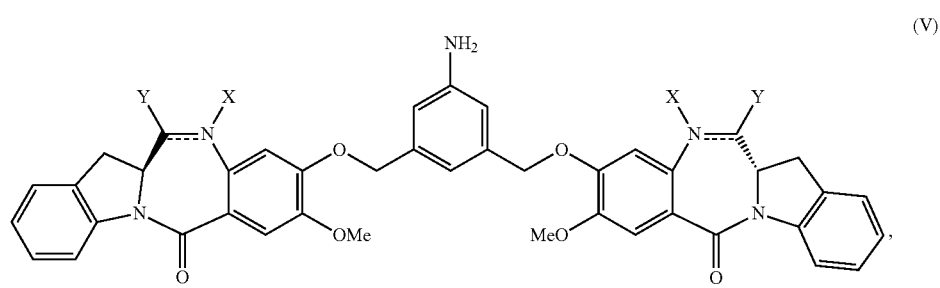

or a salt thereof; and 2) reacting the compound of formula (V) or a salt thereof, with a compound of formula (X):

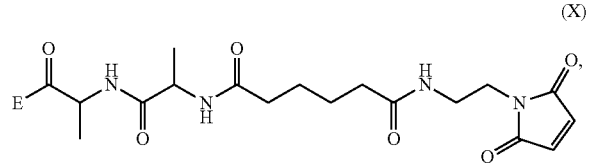
(X)

wherein:

each double line ⚌ between N and C independently represents a single bond or a double bond, provided that when it is a double bond X is absent and Y is —H, and when it is a single bond, X and Y are both —H; and E is —OH, halide or —C(═O)E is an activated ester.

Also included in the third embodiment is a method of preparing a compound of formula (dA):

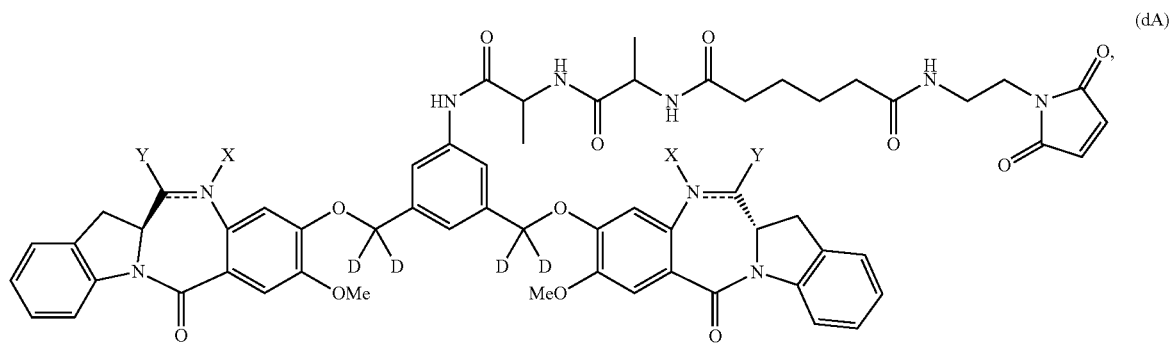
(dA)

or a salt thereof, comprising the steps of:

1) reacting a compound of formula (dIV):

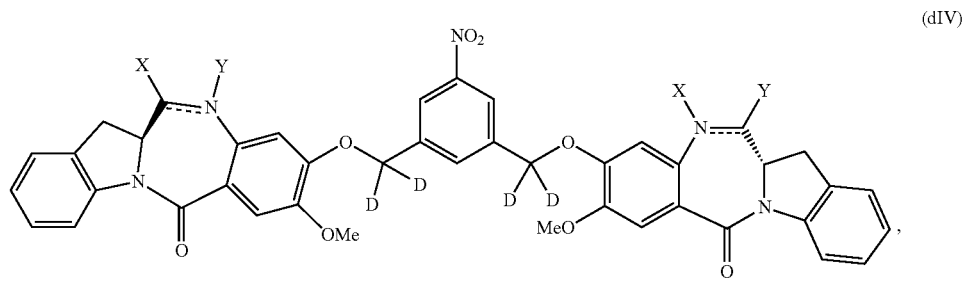
(dIV)

or a salt thereof, with a reducing agent to form a compound of formula (dV):

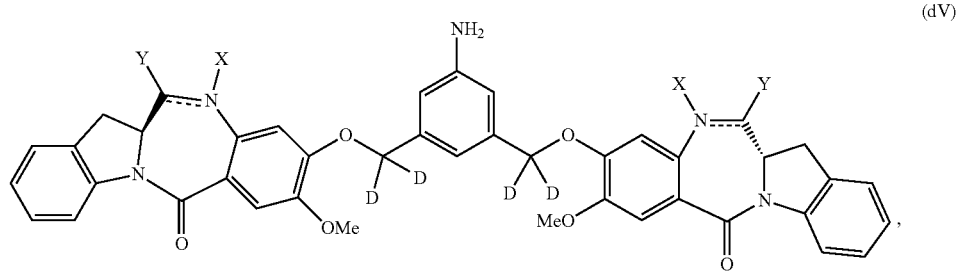
(dV)

or a salt thereof; and 2) reacting the compound of formula (dV) or a salt thereof, with a compound of formula (X):

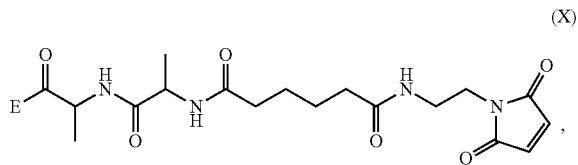

(X)

wherein the variables are the same as described for formula (A).

In certain embodiments, both double line == between N and C independently represent a double bond. In certain embodiments, both double line == between N and C independently represent a single bond.

In certain embodiments, one of the double line == between N and C represents a double bond; and the other double line == between N and C represents a single bond, the compound of formula (A) is represented by the following formula:

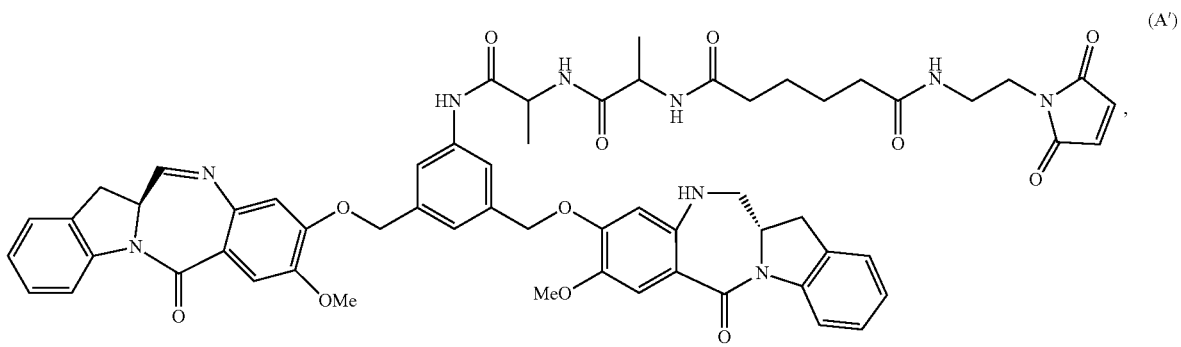 [SMILES: COc1cc2c(cc1OCc1cc(COc3cc4c(cc3OC)C(=O)N3c5ccccc5C[C@H]3CN4)cc(NC(=O)C(C)NC(=O)C(C)NC(=O)CCCCC(=O)NCCN3C(=O)C=CC3=O)c1)N=C[C@@H]1Cc3ccccc3N1C2=O]

(A')

or a salt thereof, and the compound of formula (dA) is represented by the following formula:

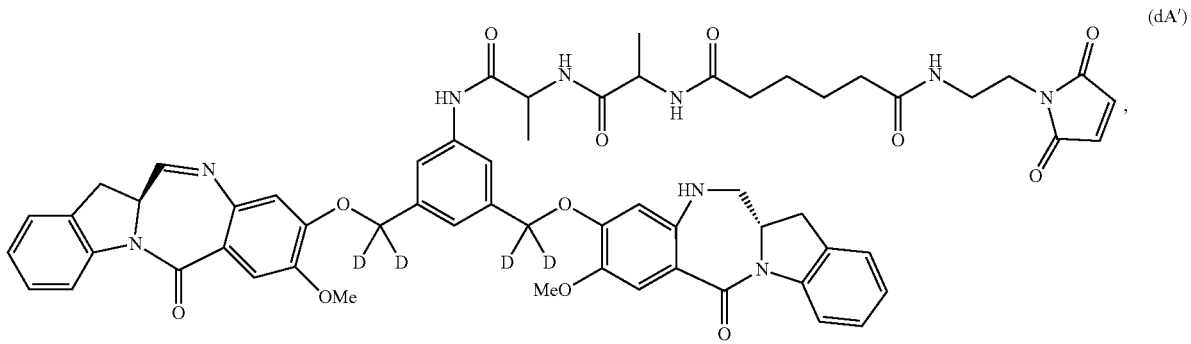 [SMILES: [2H]C([2H])(Oc1cc2c(cc1OC)C(=O)N1c3ccccc3C[C@H]1C=N2)c1cc(NC(=O)C(C)NC(=O)C(C)NC(=O)CCCCC(=O)NCCN2C(=O)C=CC2=O)cc(C([2H])([2H])Oc2cc3c(cc2OC)C(=O)N2c4ccccc4C[C@H]2CN3)c1]

(dA')

or a salt thereof.

In a fourth embodiment, for the method of the third embodiment, the compound of formula (A) or a salt thereof is represented by formula (A-1):

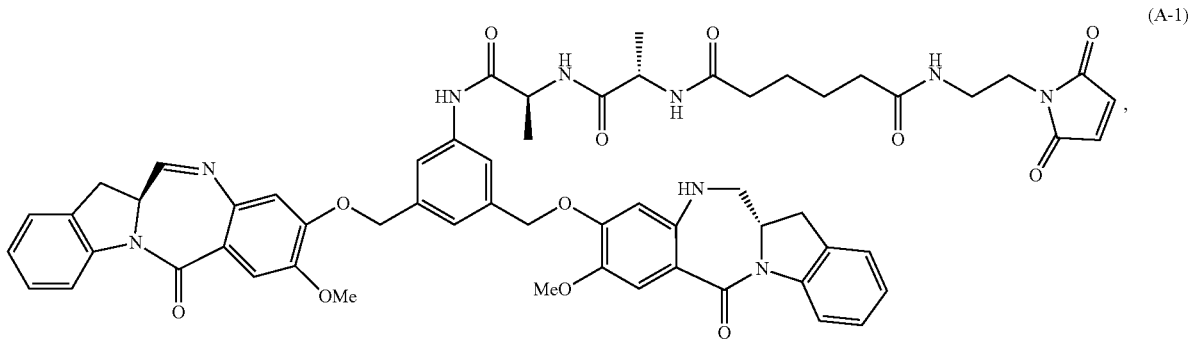 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

(A-1)

or a salt thereof, and the method comprises the steps of:
1) reacting a compound of formula (IV-1):

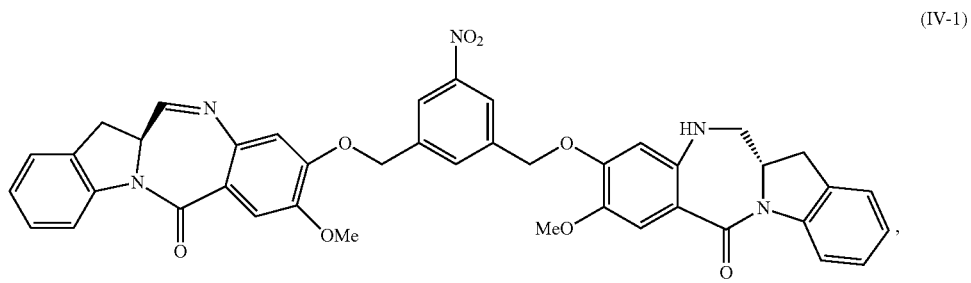 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

or a salt thereof, with a reducing agent to form a compound of formula (V-1):

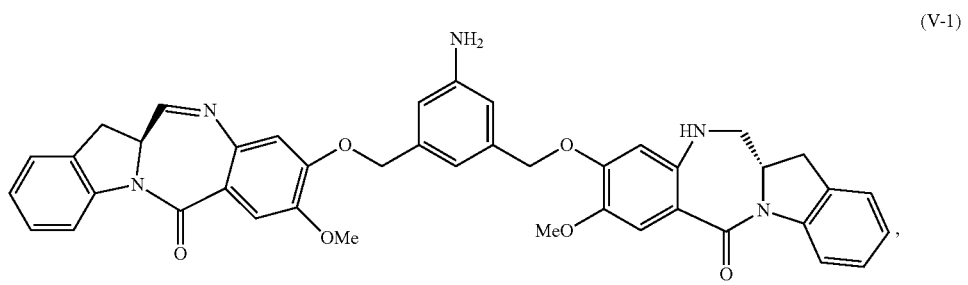 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

or a salt thereof; and
2) reacting the compound of formula (V-1) or a salt thereof, with a compound of formula (X-1):

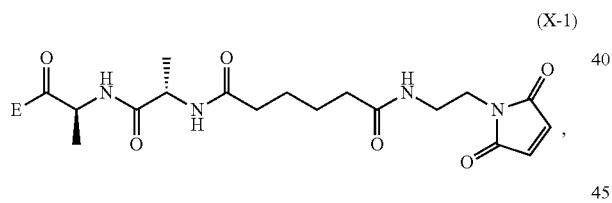

wherein E is —OH, halide or —C(=O)E is an activated ester.

Also in the fourth embodiment, for the method of the third embodiment, the compound of formula (dA) or a salt thereof is represented by formula (dA-1):

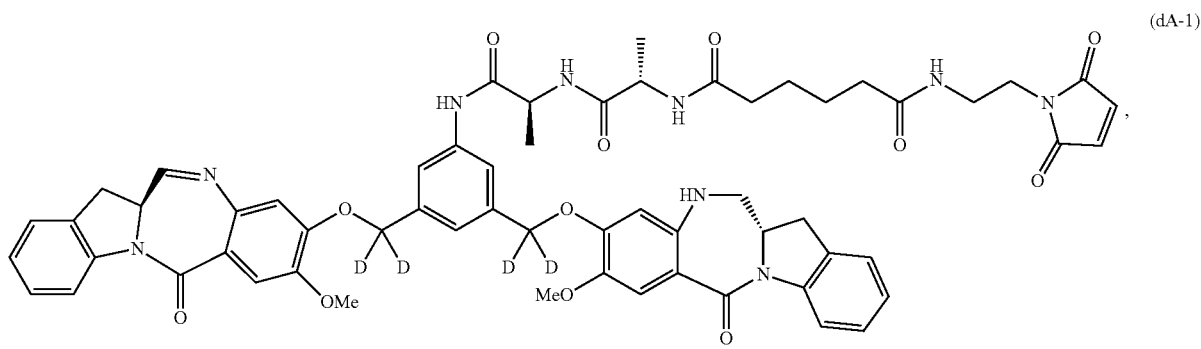 [SMILES: [2H]C([2H])(Oc1cc2c(cc1OC)C(=O)N1c3ccccc3C[C@H]1C=N2)c1cc(NC(=O)[C@H](C)NC(=O)[C@H](C)NC(=O)CCCCC(=O)NCCN2C(=O)C=CC2=O)cc(C([2H])([2H])Oc2cc3c(cc2OC)C(=O)N2c4ccccc4C[C@H]2CN3)c1]

or a salt thereof, and the method comprises the steps of:
1) reacting a compound of formula (dIV-1):

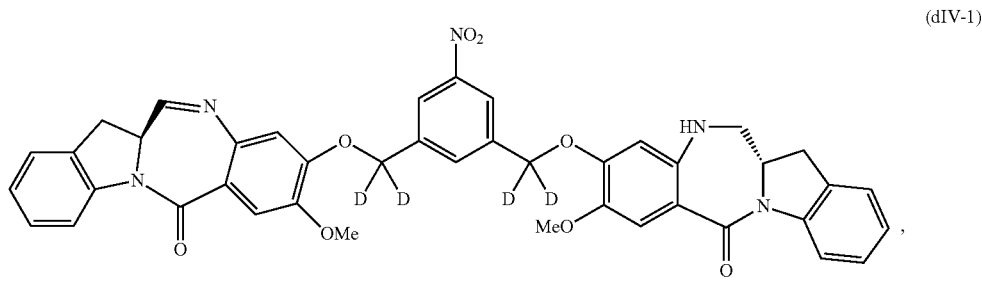 [SMILES: [2H]C([2H])(Oc1cc2c(cc1OC)C(=O)N1c3ccccc3C[C@H]1C=N2)c1cc([N+](=O)[O-])cc(C([2H])([2H])Oc2cc3c(cc2OC)C(=O)N2c4ccccc4C[C@H]2CN3)c1]

(dIV-1)

or a salt thereof, with a reducing agent to form a compound of formula (dV-1):

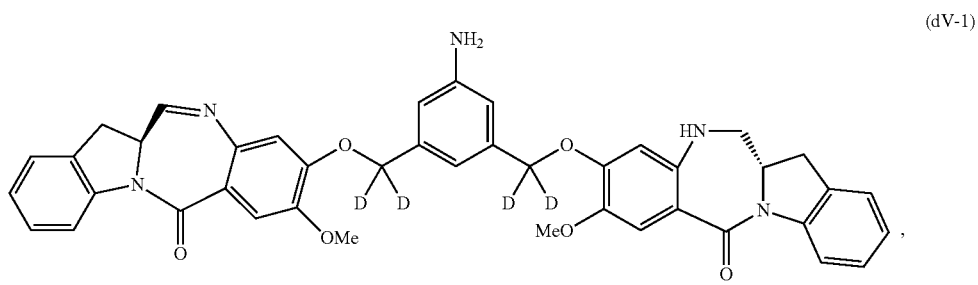 [SMILES: [2H]C([2H])(Oc1cc2c(cc1OC)C(=O)N1c3ccccc3C[C@H]1C=N2)c1cc(N)cc(C([2H])([2H])Oc2cc3c(cc2OC)C(=O)N2c4ccccc4C[C@H]2CN3)c1]

(dV-1)

or a salt thereof; and
2) reacting the compound of formula (dV-1) or a salt thereof, with a compound of formula (X-1):

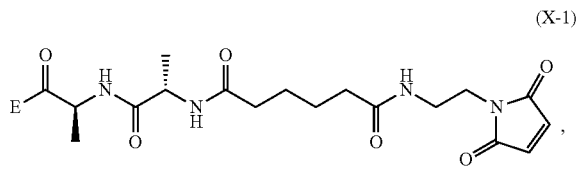

(X-1)

wherein E is —OH, halide or —C(=O)E is an activated ester

In a fifth embodiment, for the methods of the third or fourth embodiment, Any suitable reducing reagent that can convert a nitro (—$NO_2$) group to an amine (—$NH_2$) group can be used in the reaction of step 1). In certain embodiments, the reducing reagent is selected from the group consisting of: hydrogen gas, sodium hydrosulfite, sodium sulfide, stannous chloride, titanium (II) chloride, zinc, iron and samarium iodide. In certain embodiments, the reducing reagent is Fe/$NH_4Cl$, Fe/$NH_4Cl$, Zn/$NH_4Cl$, $FeSO_4$/$NH_4OH$, or Sponge Nickel. In specific embodiments, the reducing agent is Fe/$NH_4Cl$.

In certain embodiments, the reaction between the compound of formula (IV), (dIV), (IV-1) or (dIV-1) with the reducing agent is carried out in a mixture of water and one or more organic solvents. Any suitable organic solvent can be used. Exemplary organic solvents include, but are not limited to, DMF, $CH_2Cl_2$, dichloroethane, THF, dimethylacetamide, methanol, ethanol, etc. In certain embodiments, the organic solvent is THF or methanol or a combination thereof. In a specific embodiment, the reaction between the compound of formula (IV), (dIV), (IV-1) or (dIV-1) with the reducing agent is carried out in a mixture of water, THF and methanol.

In a sixth embodiment, for the methods of any one of the first, second, third, fourth or fifth embodiment, E is —OH and the reaction between the compound of formula (V) and the compound of formula (X), between the compound of formula (dV) and the compound of formula (X), between the compound of formula (V-1) and (X-1), or between the compound of formula (dV-1) and (dX-1) is carried out in the presence of an activating agent.

In certain embodiments, the activating agent is a carbodiimide, a uronium, an active ester, a phosphonium, 2-alkyl-1-alkylcarbonyl-1,2-dihydroquinoline, 2-alkoxy-1-alkoxycarbonyl-1,2-dihydroquinoline, 2,4,6-trialkyl-1,3,5,2,4,6-trioxatriphosphorinane 2,4,6-trioxide, or alkylchloroformate. In a specific embodiment, the activating agent is a carbodiimide. In a more specific embodiment, the activating agent is dicyclohexylcarbodiimide (DCC), 1-ethyl-3-(3-dimethylaminopropyl)carbodiimide (EDC), or diisopropylcarbodiimide (DIC). In another specific embodiment, the activating agent is N-ethoxycarbonyl-2-ethoxy-1,2-dihydroquinoline (EEDQ).

In certain embodiments, the reaction between the compound of formula (V) and the compound of formula (X), between the compound of formula (dV) and the compound of formula (X), between the compound of formula (V-1) and (X-1) or between the compound of formula (dV-1) and (X-1) is carried out in an organic solvent or a solvent mixture. Any suitable organic solvent described herein can be used. In certain embodiments, the organic solvent is dichloromethane or methanol or a mixture thereof.

In a seventh embodiment, the present invention provides a method preparing a compound of formula (Xa):

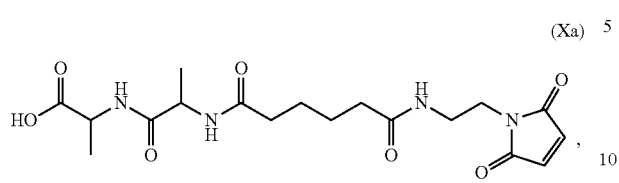

or a salt thereof, comprising reacting the compound of formula (IX):

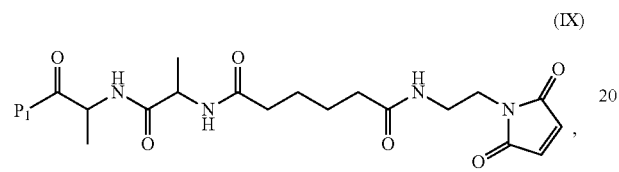

or a salt thereof, with a carboxylic acid deprotecting agent, wherein $P_1$ is a carboxylic acid protecting group.

In an eighth embodiment, for the method of the seventh embodiment, the compound of formula (Xa) is represented by formula (X-1a):

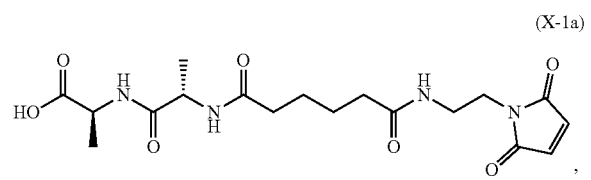 [SMILES: C[C@H](NC(=O)[C@H](C)NC(=O)CCCCC(=O)NCCN1C(=O)C=CC1=O)C(=O)O]

or a salt thereof, and the method comprises reacting the compound of formula (IX-1):

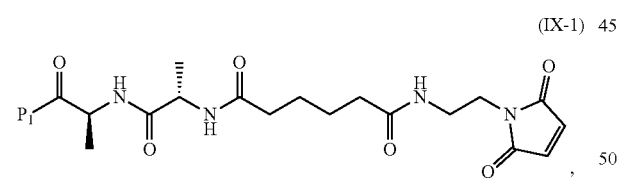

or a salt thereof, with a carboxylic acid deprotecting agent, wherein $P_1$ is a carboxylic acid protecting group.

In a ninth embodiment, the present invention provides a method of preparing a compound of formula (IX):

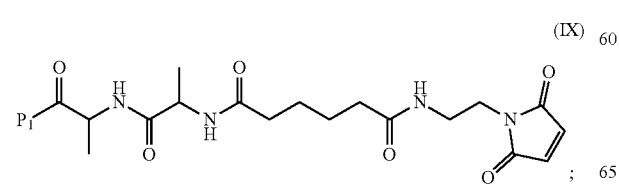

comprising reacting a compound of formula (VIII):

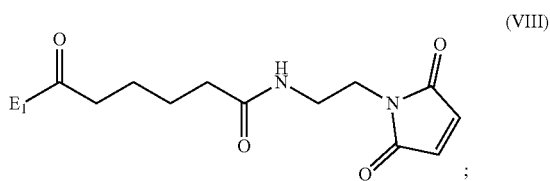

or a salt thereof, with a compound of formula (c):

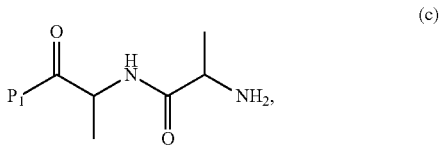

or a salt thereof, wherein $E_1$ is —OH, halide or —C(=O)$E_1$ is an activated ester; and $P_1$ is an carboxylic acid protecting group.

In a tenth embodiment, the compound of formula (IX) or a salt thereof is represented by formula (IX-1):

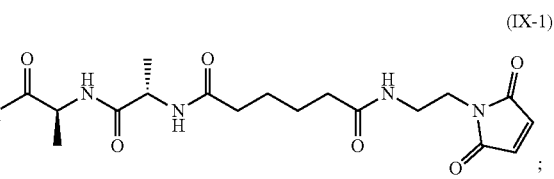

or a salt thereof, and the method comprises reacting a compound of formula (VIII):

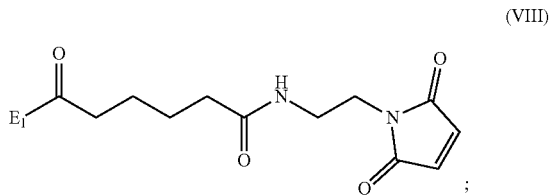

or a salt thereof, with a compound of formula (c-1):

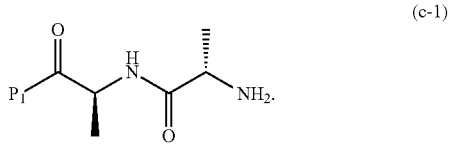

or a salt thereof, wherein $E_1$ is —OH, halide or —C(=O)$E_1$ is an activated ester; and $P_1$ is a carboxylic acid protecting group.

In a eleventh embodiment, the present invention provides a method of preparing a compound of formula (Xa):

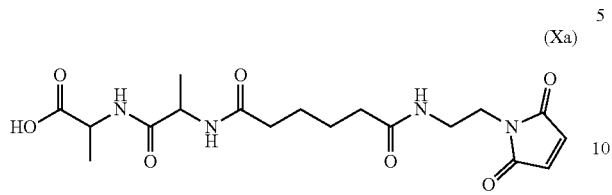
(Xa)

or a salt thereof, comprising the steps of:

1) reacting a compound of formula (VIII):

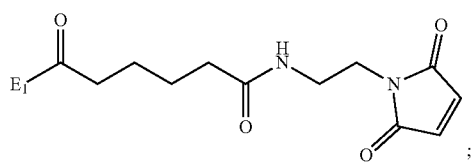
(VIII)

or a salt thereof, with a compound of formula (c):

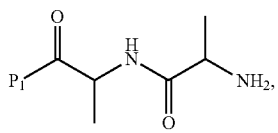
(c)

or a salt thereof, to form a compound of formula (IX):

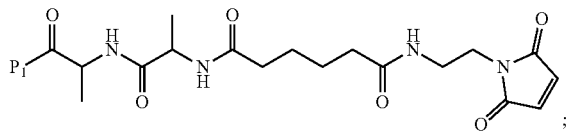
(IX)

and 2) reacting the compound of formula (IX) with a carboxylic acid deprotecting agent, wherein $E_1$ is —OH, halide or —C(=O)$E_1$ is an activated ester; and $P_1$ is a carboxylic acid protecting group.

In a twelfth embodiment, the compound of formula (Xa) or a salt thereof is represented by formula (X-1a):

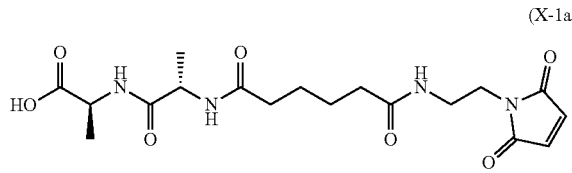
(X-1a)

or a salt thereof, comprising the steps of:

1) reacting a compound of formula (VIII):

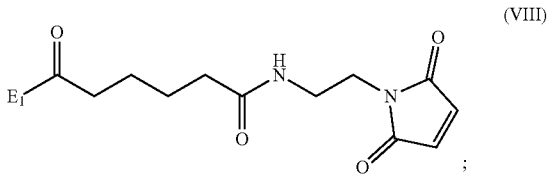
(VIII)

or a salt thereof, with a compound of formula (c-1):

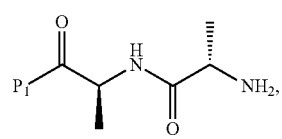
(c-1)

or a salt thereof, to form a compound of formula (IX-1):

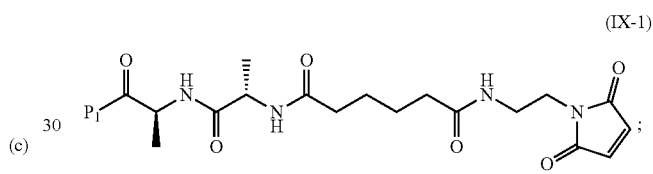
(IX-1)

and 2) reacting the compound of formula (IX-1) with a carboxylic acid deprotecting agent, wherein $E_1$ is —OH, halide or —C(=O)$E_1$ is an activated ester; and $P_1$ is a carboxylic acid protecting group.

In certain embodiments, for the method of the seventh, eighth, ninth, tenth, eleventh or twelfth embodiment, the carboxylic acid protecting group represented by $P_1$ can be any suitable carboxylic acid protecting group known in the art. In certain embodiments, the carboxylic acid protecting group include, but are not limited to alkyl ester (e.g., methyl ester or tert-butyl ester), benzyl ester, thioester (e.g., tert-butyl thioester), silyl ester (e.g., trimethylsilyl ester), 9-fluorenylmehtyl ester, (2-trimethylsilyl)ethoxymethyl ester, 2-(trimethylsilyl)ethyl ester, diphenylmethyl ester or oxazoline. In certain embodiments, the carboxylic acid protecting group is methyl ester, tert-butyl ester, benzyl ester or trimethylsilyl ester, i.e., $P_1$ is —OMe, —O$^t$Bu, —OBn, —O-silyl (e.g., —OSi(Me)$_3$). In certain embodiments, the carboxylic acid protecting group is tert-butyl ester, i.e., $P_1$ is —O$^t$Bu.

To deprotect the carboxylic acid protecting group, any suitable deprotecting agent known in the art can be used. The suitable deprotecting agent depends on the identity of the carboxylic acid protecting group. For example, when $P_1$ is —O$^t$Bu, the protecting group can be removed by the treatment with an acid, a base or a suitable reductant. In certain embodiments, an acid can be used to remove the tert-butyl ester protecting group. Exemplary acids include, but are not limited to, formic acid, acetic acid, trifluoroacetic acid, hydrochloric acid, and phosphoric acid. In a specific embodiment, trifluoroacetic acid is used as the deprotecting agent.

In certain embodiments, the deprotection reaction can be carried in any suitable organic solvent(s). Exemplary organic solvents include, but are not limited to, DMF, $CH_2Cl_2$, dichloroethane, THF, dimethylacetamide, methanol, ethanol, etc. In certain embodiments, the deprotection reaction is carried out in dichloromethane.

In certain embodiments, for method of the ninth, tenth, eleventh or twelfth embodiment, $E_1$ is —OH and the reaction between the compound of formula (VIII) and the compound of formula (c) or the compound of formula (c-1) is carried out in the presence of an activating agent.

In certain embodiments, the activating agent is a carbodiimide, a uronium, an active ester, a phosphonium, 2-alkyl-1-alkylcarbonyl-1,2-dihydroquinoline, 2-alkoxy-1-alkoxy-carbonyl-1,2-dihydroquinoline, 2,4,6-trialkyl-1,3,5,2,4,6-trioxatriphosphorinane 2,4,6-trioxide, or alkylchloroformate. In a specific embodiment, the activating agent is 2,4,6-trialkyl-1,3,5,2,4,6-trioxatriphosphorinane 2,4,6-trioxide. In a more specific embodiment, the activating agent is 2,4,6-tripropyl-1,3,5,2,4,6-trioxatriphosphorinane 2,4,6-trioxide. In certain embodiments, the reaction between the compound of formula (VIII) and the compound of formula (c) or the compound of formula (c-1) is carried out in the presence of a base. In certain embodiments, the base is a non-nucleophilic base. Exemplary non-nucleophilic bases include, but are not limited to, triethylamine, imidazole, diisopropylethylamine, pyridine, 2,6-lutidine, dimethylformamide, 1,8-diazabicyclo[5.4.0]undec-7-ene (DBU), or tetramethylpiperidine. In a specific embodiment, the base is triethylamine or diisopropylethylamine. In another specific embodiment, the base is diisopropylethylamine In certain embodiments, the reaction between the compound of formula (VIII) and the compound of formula (c) or the compound of formula (c-1) is carried out in the presence of an activating agent described above and a base described above. In certain embodiments, the reaction is carried out in the presence of 2,4,6-tripropyl-1,3,5,2,4,6-trioxatriphosphorinane 2,4,6-trioxide and triethylamine or diisopropylethylamine. In a specific embodiment, the reaction is carried out in the presence of 2,4,6-tripropyl-1,3,5,2,4,6-trioxatriphosphorinane 2,4,6-trioxide and diisopropylethylamine Any suitable organic solvents can be used for the reaction the reaction between the compound of formula (VIII) and the compound of formula (c) or the compound of formula (c-1). In certain embodiments, the reaction is carried out in dichloromethane In a thirteenth embodiment, for the method of the ninth, tenth, eleventh, or twelfth embodiment, the compound of formula (VIII) is represented by formula (VIIIa):

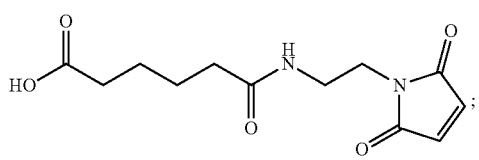

(VIIIa)

and the compound of formula (VIIIa) or a salt thereof is prepared by a method comprising the steps of:
a) reacting a compound of formula (VI):

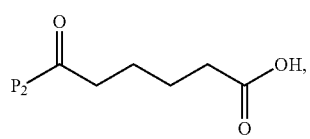

or a salt thereof, with a compound of formula (d):

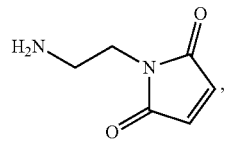

(d)

or a salt thereof, to form a compound of formula (VII):

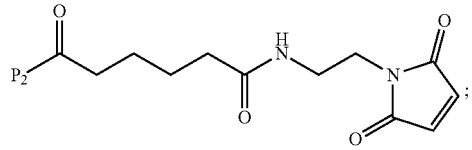

(VII)

and
b) reacting the compound of formula (VII) with a carboxylic acid deprotecting agent to form the compound of formula (VIIIa) or a salt thereof, wherein $P_2$ is a carboxylic acid protecting group.

Any suitable carboxylic acid protecting group can be used. In certain embodiments, the carboxylic acid protecting group include, but are not limited to alkyl ester (e.g., methyl ester or tert-butyl ester), benzyl ester, thioester (e.g., tert-butyl thioester), silyl ester (e.g., trimethylsilyl ester), 9-fluorenylmehtyl ester, (2-trimethylsilyl)ethoxymethyl ester, 2-(trimethylsilyl)ethyl ester, diphenylmethyl ester or oxazoline. In certain embodiments, the carboxylic acid protecting group is methyl ester, tert-butyl ester, benzyl ester or trimethylsilyl ester, i.e., $P_2$ is —OMe, —O$^t$Bu, —OBn, —O-silyl (e.g., —OSi(Me)$_3$). In certain embodiments, the carboxylic acid protecting group is tert-butyl ester, i.e., $P_2$ is —O$^t$Bu.

To deprotect the carboxylic acid protecting group, any suitable carboxylic deprotecting agent known in the art can be used. Suitable deprotecting agents depend on the identity of the carboxylic acid protecting group. For example, when $P_2$ is —O$^t$Bu, the protecting group can be removed by the treatment with an acid, a base or a suitable reductant. In certain embodiments, an acid can be used to remove the tert-butyl ester protecting group. Exemplary acids include, but are not limited to, formic acid, acetic acid, trifluoroacetic acid, hydrochloric acid, and phosphoric acid. In a specific embodiment, trifluoroacetic acid is used as the carboxylic acid deprotecting agent.

In certain embodiments, the deprotection reaction can be carried in any suitable organic solvent(s). Exemplary organic solvents include, but are not limited to, DMF, $CH_2Cl_2$, dichloroethane, THF, dimethylacetamide, methanol, ethanol, etc. In certain embodiments, the deprotection reaction is carried out in dichloromethane.

In certain embodiments, the reaction between the compound of formula (VI) and the compound of formula (d) is carried out in the presence of an activating agent. Any suitable activating agent described herein can be used. In certain embodiments, the activating agent is 2,4,6-trialkyl-1,3,5,2,4,6-trioxatriphosphorinane 2,4,6-trioxide. In a more specific embodiment, the activating agent is 2,4,6-tripropyl-1,3,5,2,4,6-trioxatriphosphorinane 2,4,6-trioxide.

Any suitable organic solvents can be used for the reaction the reaction between the compound of formula (VI) and the compound of formula (d). In certain embodiments, the reaction is carried out in dichloromethane.

In a fourteenth embodiment, the present invention provides a method of preparing a compound of formula (II),

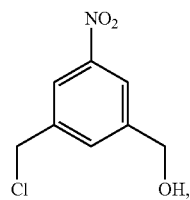

comprising reacting a compound of formula (I):

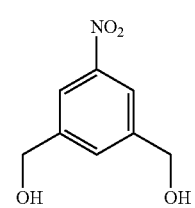

with hydrochloric acid in toluene.

Also included in the fourteenth embodiment is a method of preparing a compound of formula (dII),

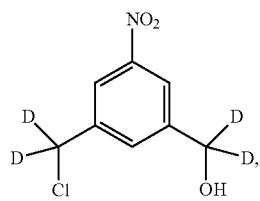

comprising reacting a compound of formula (dI):

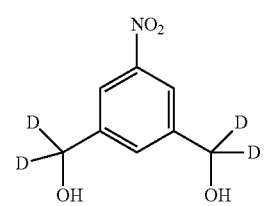

with hydrochloric acid in toluene.

In a fifteenth embodiment, the present invention provides a method of preparing a compound of formula (IV-1):

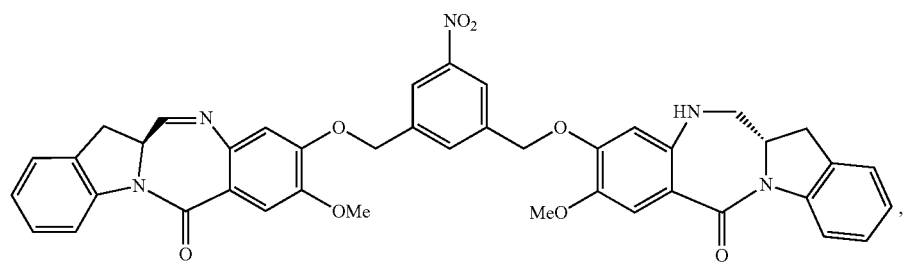

or a salt thereof, comprising the steps of:
1) reacting a compound of formula (I):

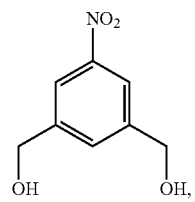

with hydrochloric acid in toluene to form a compound of formula (II):

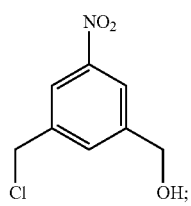

2) reacting the compound of formula (II) with a monomer compound of formula (a),

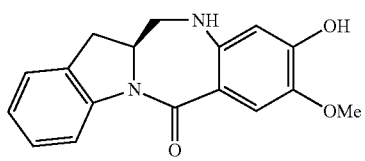

to form a compound of formula (III):

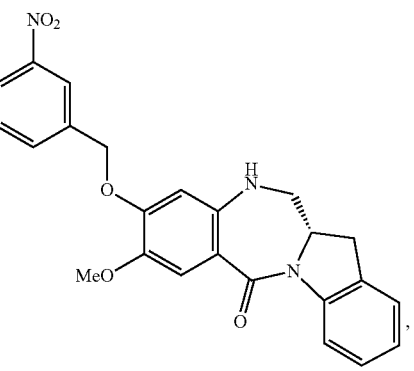

or a salt thereof;

3) reacting the compound of formula (III) or a salt thereof with a monomer compound of formula (b):

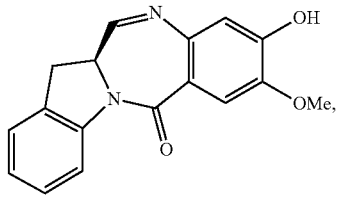
(b)

to form the compound of formula (IV-1) or a salt thereof.

Also included in the fifteenth embodiment is a method of preparing a compound of formula (dIV-1):

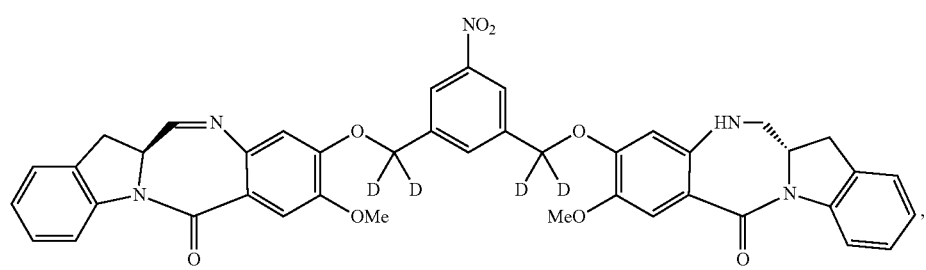
(dIV-1)

or a salt thereof, comprising the steps of:

1) reacting a compound of formula (dI):

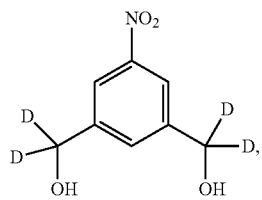
(dI)

with hydrochloric acid in toluene to form a compound of formula (dII):

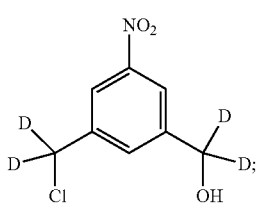
(dII)

2) reacting the compound of formula (dII) with a monomer compound of formula (a),

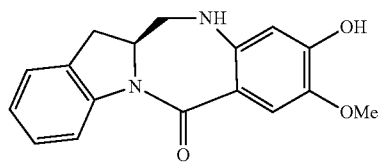
(a)

to form a compound of formula (dIII):

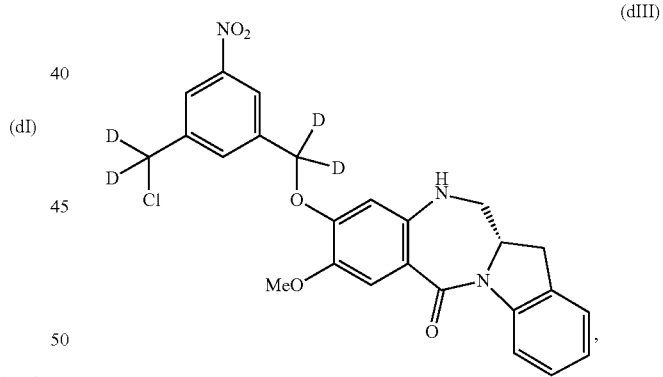
(dIII)

or a salt thereof;

3) reacting the compound of formula (dIII) or a salt thereof with a monomer compound of formula (b):

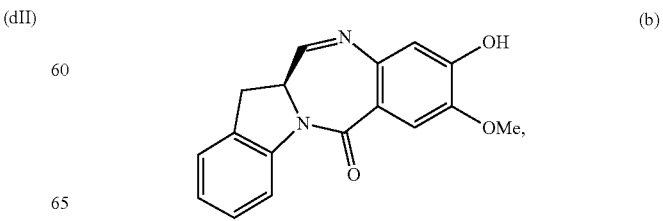
(b)

to form the compound of formula (dIV-1) or a salt thereof.

In a sixteenth embodiment, the present invention provides a method of preparing a compound of formula (A-1):

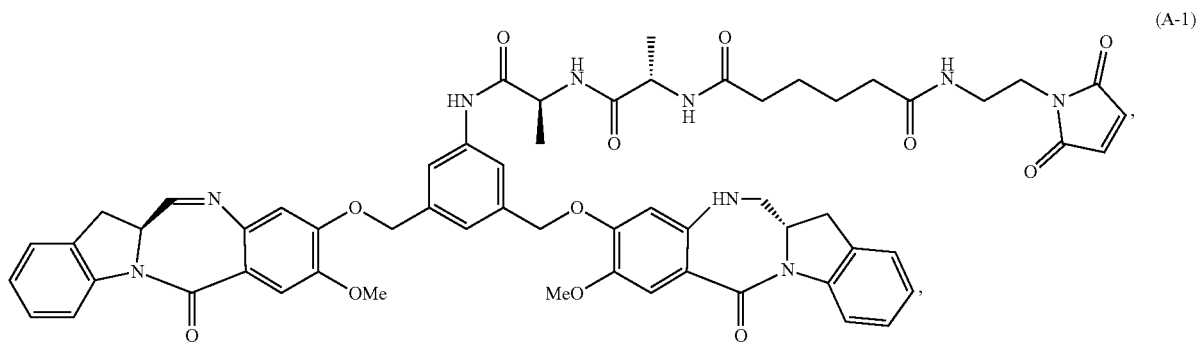 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

or a salt thereof, comprising the steps of:
1) reacting a compound of formula (I):

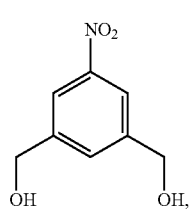

with hydrochloric acid in toluene to form a compound of formula (II):

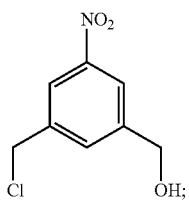

2) reacting the compound of formula (II) with a monomer compound of formula (a),

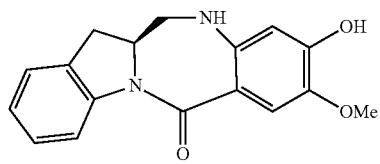

to form a compound of formula (III):

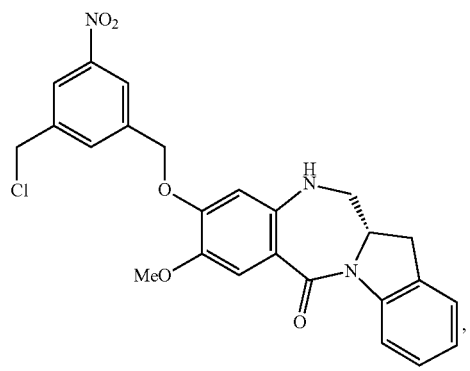

or a salt thereof;

3) reacting the compound of formula (III) or a salt thereof with a monomer compound of formula (b):

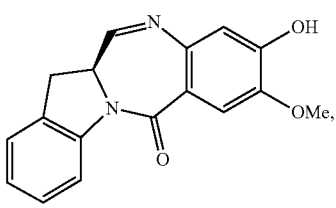

to form a compound of formula (IV-1):

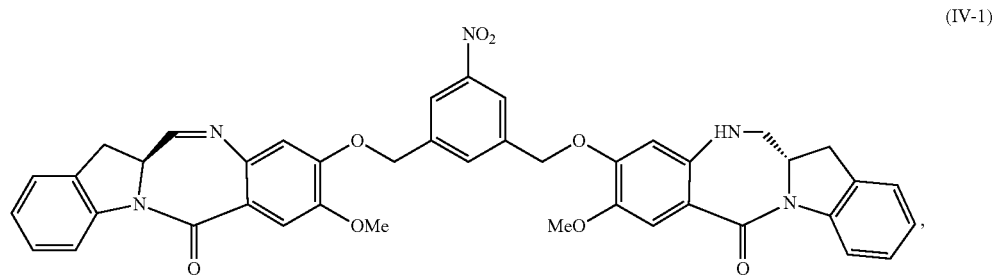 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

or a salt thereof;
4) reacting the compound of formula (IV-1) or a salt thereof with a reducing agent to form a compound of formula (V-1):

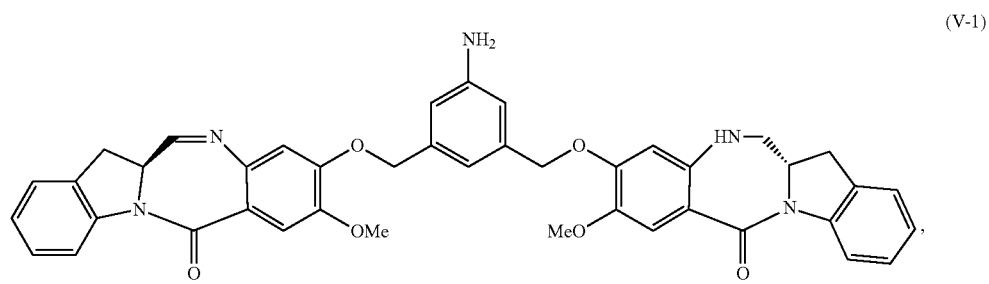 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

or a salt thereof; and
5) reacting the compound of formula (V-1) or a salt thereof, with a compound of formula (X-1):

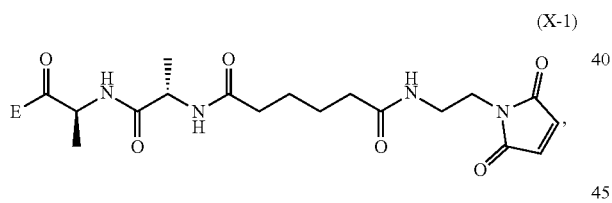

to form the compound of formula (A-1) or a salt thereof, wherein E is —OH, halide or —C(=O)E is an activated ester.

Also included in the sixteenth embodiment is a method of preparing a compound of formula (dA-1):

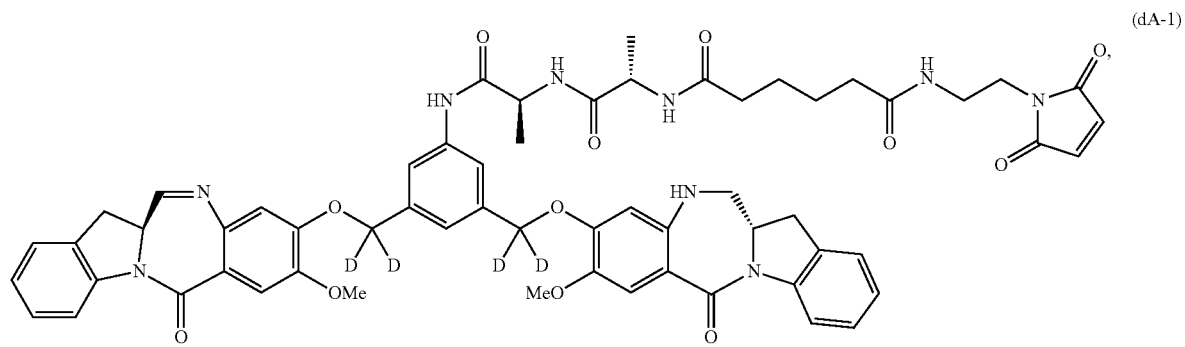 [SMILES: [2H]C([2H])(Oc1cc2c(cc1OC)C(=O)N1c3ccccc3C[C@H]1C=N2)c1cc(NC(=O)[C@H](C)NC(=O)[C@H](C)NC(=O)CCCCC(=O)NCCN2C(=O)C=CC2=O)cc(C([2H])([2H])Oc2cc3c(cc2OC)C(=O)N2c4ccccc4C[C@H]2CN3)c1]

or a salt thereof, comprising the steps of:
1) reacting a compound of formula (dI):

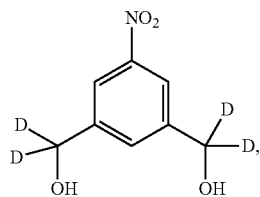
(dI)

with hydrochloric acid in toluene to form a compound of formula (dII):

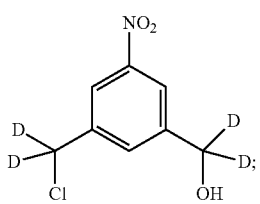
(dII)

2) reacting the compound of formula (dII) with a monomer compound of formula (a),

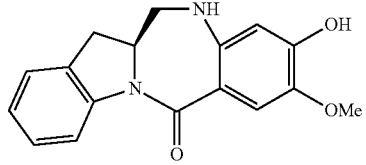
(a)

to form a compound of formula (dIII):

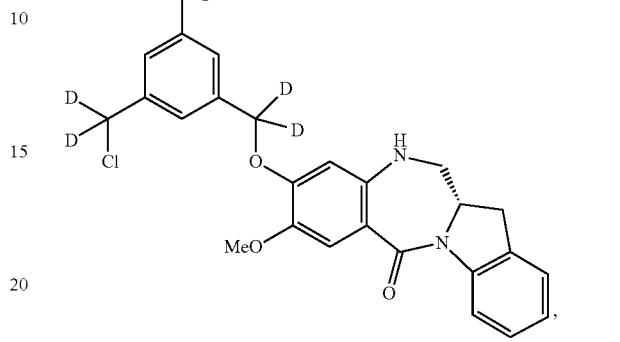
(dIII)

or a salt thereof;

3) reacting the compound of formula (dIII) or a salt thereof with a monomer compound of formula (b):

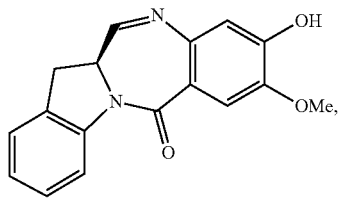
(b)

to form a compound of formula (dIV-1):

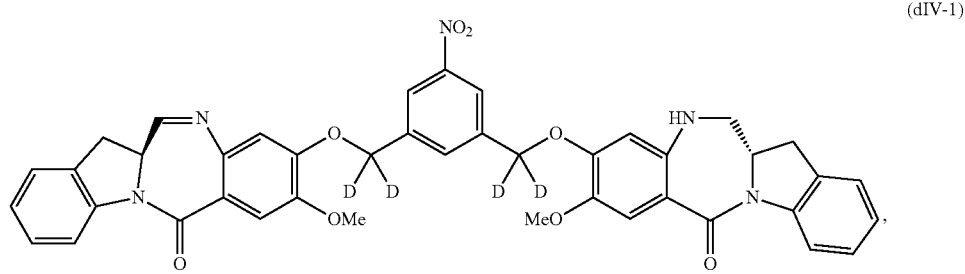 [SMILES: [2H]C([2H])(Oc1cc2c(cc1OC)C(=O)N1c3ccccc3C[C@H]1C=N2)c1cc([N+](=O)[O-])cc(C([2H])([2H])Oc2cc3c(cc2OC)C(=O)N2c4ccccc4C[C@H]2CN3)c1]
(dIV-1)

or a salt thereof;

4) reacting the compound of formula (dIV-1) or a salt thereof with a reducing agent to form a compound of formula (dV-1):

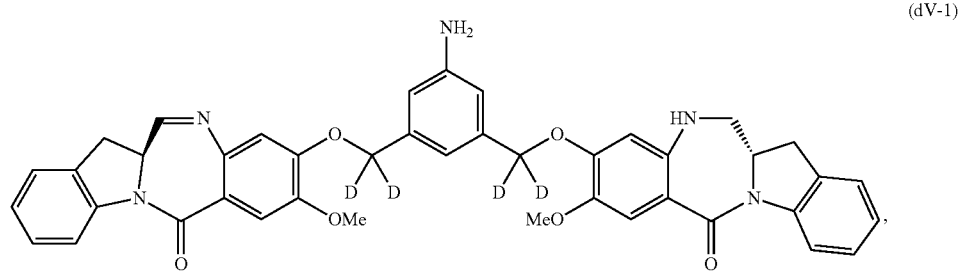 [SMILES: [2H]C([2H])(Oc1cc2c(cc1OC)C(=O)N1c3ccccc3C[C@H]1C=N2)c1cc(N)cc(C([2H])([2H])Oc2cc3c(cc2OC)C(=O)N2c4ccccc4C[C@H]2CN3)c1]

or a salt thereof; and 5) reacting the compound of formula (dV-1) or a salt thereof, with a compound of formula (X-1):

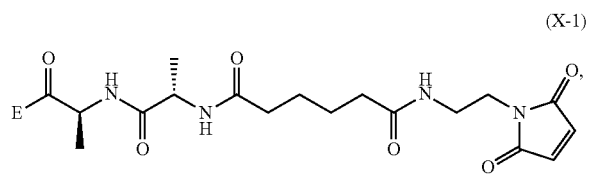

to form the compound of formula (dA-1) or a salt thereof, wherein E is —OH, halide or —C(=O)E is an activated ester.

In a seventeenth embodiment, for the method of the fourteenth, fifteenth or sixteenth embodiment, the compound of formula (I) or (dI) is reacted with concentrated hydrochloric acid to form the compound of formula (II) or (dII) respectively. For example, 30-38 w/w % of hydrochloric acid can be used.

In certain embodiments, the reaction between the compound of formula (I) or (dI) and hydrochloric acid is carried out at a temperature between 30° C. and 110° C., between 40° C. and 105° C., between 50° C. and 100° C., between 60° C. and 100° C., between 70° C. and 100° C., between 80° C. and 100° C. or between 90° C. and 100° C. In certain embodiments, the reaction is carried out at 95° C.

The reaction between the compound of formula (I) or (dI) and hydrochloric acid can be carried out until the reaction is in substantial completion. For example, the reaction can be carried out between 5 minutes to 1 week, between 5 minutes to 72 hours, between 1 hour to 48 hours, between 1 hour to 12 hours, between 6 hours to 18 hours, or between 1 hour to 6 hours.

In certain embodiments, the compound of formula (II) or (dII) obtained from the reaction of the compound of formula (I) or (dI) and hydrochloric acid is purified. The compound of formula (II) or (dII) can be purified by column chromatography or crystallization. In certain embodiments, the compound of formula (II) or (dII) is purified by crystallization. In a specific embodiment, the compounds of formula (II) or (dII) is crystalized in toluene. For example, the compound of formula (II) or (dII) is crystalized by dissolving the compound in hot toluene followed by cooling until the compound crystallized out the solution.

In a eighteenth embodiment, for methods of the fifteenth, sixteenth or seventeenth embodiment, the compound of formula (II) or (dII) is reacted with the monomer compound of formula (a) in the presence of an alcohol activating agent.

Any suitable alcohol activating agent can be used. In certain embodiments, the alcohol activating agent is a trialkylphosphine, triarylphosphine, or triheteroarylphosphine. In a specific embodiment, the alcohol activating agent is trimethylphosphine, tributylphosphine, tri(o-tolyl)phosphine, tri(m-tolyl)phosphine, tri(p-tolyl)phosphine, tri(2-pyridyl)phosphine, tri(3-pyridyl)phosphine, tri(4-pyridyl)phosphine, or [4-(3,3,4,4,5,5,6,6,7,7,8,8,9,9,10,10,10-heptadecafluorodecyl)phenyl]diphenylphosphine. In another embodiment, the alcohol activating agent can be a phosphine-like reagent, such as (tributylphosphoranylidene)acetonitrile, (cyanomethylene)tributylphosphorane (CMBP), or (cyanomethylene)trimethylphosphorane (CMMP). In a more specific embodiment, the alcohol activating agent is triphenylphosphine. In yet another more specific embodiment, the alcohol is tributylphosphine. In one embodiment, the alcohol activating agent can be polymer-bound or polymer-supported, such as polymer-bound or polymer-supported trialkyl phosphine, triarylphosphine (e.g., triphenylphosphine), or triheteroarylphosphine.

In certain embodiments, for the method described in the eighteenth embodiment, the compound of formula (II) or (dII) is reacted with the monomer compound of formula (a) the presence of an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis (2,2,2-trichloroethyl) azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl)azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In a specific embodiment, for methods of the eighteenth embodiment, the compound of formula (II) or (dII) is reacted with the monomer compound of formula (a) in the presence of tributylphosphine or triphenylphosphine and an azodicarboxylate. In one embodiment, the azodicarboxylate is selected from the group consisting of: diethyl azodicarboxylate (DEAD), diisopropyl azodicarboxylate (DIAD), 1,1'-(azodicarbonyfldipiperidine (ADDP), and ditertbutyl azodicarboxylate (DTAD). More specifically, the azodicarboxylate is DIAD. In a more specific embodiment, the compound of formula (II) or (dII) is reacted with the monomer compound of formula (a) in the presence of tributylphosphine and DIAD.

In certain embodiments, the alcohol activating agent and the azodicarboxylate is mixed together to form an alcohol activating agent-azodicarboxylate complex. The compound of formula (II) or (dII) is mixed with the complex first before contacting with the monomer compound of formula (a).

In certain embodiments, the reaction of the eighteenth embodiment described above can be carried out in an organic solvent(s). Any suitable organic solvent(s) described herein can be used. In certain embodiments, the organic solvent is THF.

In a nineteenth embodiment, for the method of the fifteenth, sixteenth, seventeenth, or eighteenth embodiment, in step 3) of the method, the compound of formula (III) or (dIII) or a salt thereof is reacted with the monomer compound of formula (b) in the presence of a base. In certain embodiments, the base is sodium carbonate, potassium carbonate, cesium carbonate, sodium hydride, or potassium hydride. Preferably, the base is potassium carbonate.

In certain embodiments, the reaction between the compound of formula (III) or (dIII) or a salt thereof and the monomer compound of formula (b) further comprises potassium iodide.

In certain embodiments, the reaction between the compound of formula (III) or (dIII) or a salt thereof and the monomer compound of formula (b) is carried out in the presence of potassium carbonate and potassium iodide.

Any suitable organic solvents can be used for the methods of the twentieth embodiment. In one embodiment, the solvent is a polar aprotic solvent. Exemplary solvents include, but are not limited to, dimethylformamide (DMF), $CH_2Cl_2$, dichloroethane, THF, dimethylacetamide, etc. In certain embodiments, dimethylformamide or dimethylacetamide is used as the solvent.

In a twentieth embodiment, for the method of the fifteenth, sixteenth, seventeenth, eighteenth, or nineteenth embodiment, in the reaction of step 4), the reducing reagent is selected from the group consisting of: hydrogen gas, sodium hydrosulfite, sodium sulfide, stanneous chloride, titanium (II) chloride, zinc, iron and samarium iodide. In certain embodiments, the reducing reagent is Fe/$NH_4Cl$, Fe/$NH_4Cl$, Zn/$NH_4Cl$, $FeSO_4$/$NH_4OH$, or Sponge Nickel. In specific embodiments, the reducing agent is Fe/$NH_4Cl$.

In certain embodiments, the reaction between the compound of formula (IV-1) or (dIV-1) with the reducing agent is carried out in a mixture of water and one or more organic solvents. Any suitable organic solvent can be used. Exemplary organic solvents include, but are not limited to, DMF, $CH_2Cl_2$, dichloroethane, THF, dimethylacetamide, methanol, ethanol, etc. In certain embodiments, the organic solvent is THF or methanol or a combination thereof. In a specific embodiment, the reaction between the compound of formula (IV-1) or (dIV-1) with the reducing agent is carried out in a mixture of water, THF and methanol.

In some embodiments, for the methods described above, the compound of formula (dIII) can be prepared by an alternative process comprising the steps of:

a) introducing an alcohol protecting group onto one of the primary alcohols of a compound of formula (dI):

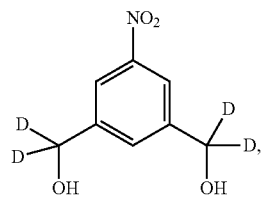

by reacting the compound of formula (dI) with an alcohol protecting agent to form a compound of formula (dI1):

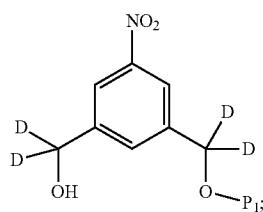

b) reacting the compound of formula (dI1) with a chlorinating agent to form a compound of formula (dI2):

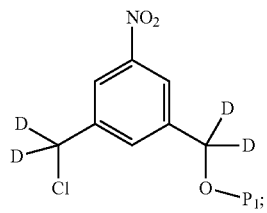

c) reacting the compound of formula (dI2) with an alcohol deprotecting agent to form a compound of formula (dI3):

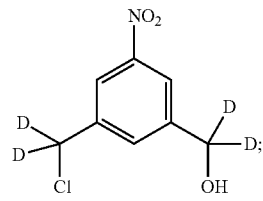

and d) reacting the compound of formula (dI3) with a sulfonating agent to form a compound of formula (dI4):

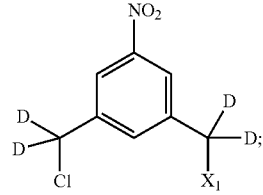

and e) reacting the compound of (dI4) with a monomer compound of formula (a),

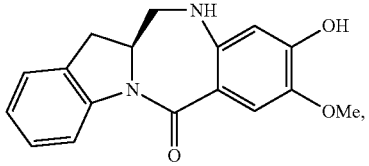
(a)

to form the compound of formula (dIII), wherein $P_1$ is an alcohol protecting group and $X_1$ is a sulfonate ester.

In one embodiment, $P_1$ is a silyl protecting group. Exemplary silyl protecting group include, but are not limited to dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. In one embodiment, $P_1$ is the silyl protecting group is triethylsilyl, triisopropylsilyl, or tert-butyldimethylsilyl. In another embodiment, $P_1$ is tert-butyldimethylsilyl.

In one embodiment, the silyl protecting group is introduced by reacting the compound of formula (dI) with R—Cl, R—Br, R—I or R—OSO$_2$CF$_3$ in the presence of a base, wherein R is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, or tert-butyldiphenylsilyl. In one embodiment, the base is a non-nucleophilic base, such as imidazole, triethylamine, diisopropylethylamine, pyridine, 2,6-lutidine, 1,8-diazabicycloundec-7-ene, or tetramethylpiperidine.

In one embodiment, the chlorinating reagent is selected from the group consisting of carbon tetrachloride, methanesulfonyl chloride, sulfuryl chloride, thionyl chloride, cyanuric chloride, N-chlorosuccinimide, phosphorus(V) oxychloride, phosphorus pentachloride, and phosphorus trichloride. In one embodiment, the chlorinating reagent is methanesulfonyl chloride.

In one embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, periodic acid. In one embodiment, the alcohol deprotecting reagent is hydrogen fluoride pyridine.

In one embodiment, $X_1$ is mesylate, tosylate, brosylate, or triflate. In another embodiment, $X_1$ is mesylate.

In one embodiment, the sulfonating reagent is methanesulfonyl anhydride, methanesulfonyl chloride, p-toluenesulfonyl chloride, 4-bromobenzenesulfonyl chloride, or trifluoromethanesulfonyl anhydride. In one embodiment, the sulfonating reagent is methanesulfonyl anhydride.

In one embodiment, the alternative process for making the compound of formula (dIII) comprises the steps of:

a) reacting the compound of formula (dI) with tert-butylchlorodimethylsilane to form a compound of formula (dI1'):

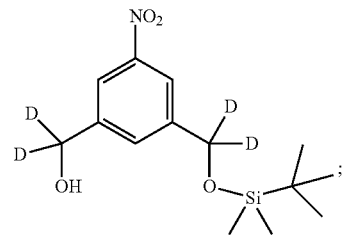
(dI1')

b) reacting the compound of formula (dI1') with methanesulfonyl chloride to form a compound of formula (dI2'):

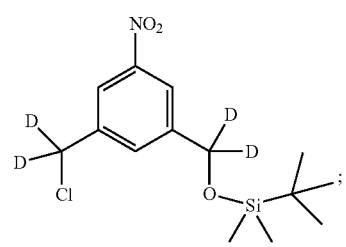
(dI2')

c) reacting the compound of formula (dI2') with an alcohol deprotecting agent to form a compound of formula (dI3):

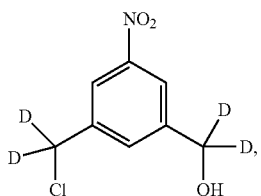
(dI3)

wherein the alcohol deprotecting agent is HF-pyridine;

d) reacting the compound of formula (dI3) with methanesulfonic anhydride or methanesufonyl chloride to form a compound of formula (dI4'):

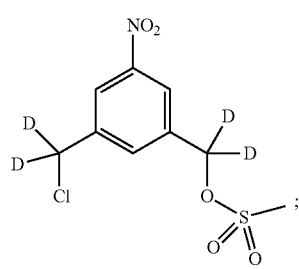
(dI4')

and e) reacting the compound of (dI4') with a monomer compound of formula (a),

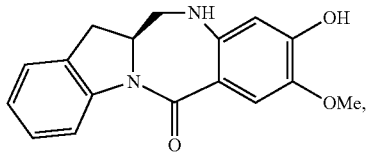
(a)

in the presence of a base (e.g., sodium carbonate or potassium carbonate) to form the compound of formula (dIII).

In a twenty-first embodiment, for the method of the sixteenth, seventeenth, eighteenth, nineteenth, or twentieth embodiment, the compound of formula (X-1) is represented by formula (X-1a):

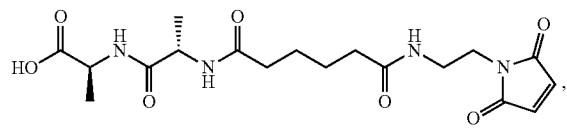
(X-1a)

and the compound of formula (X-1a) or a salt thereof is prepared by a method comprising the steps of:

a) reacting a compound of formula (VI):

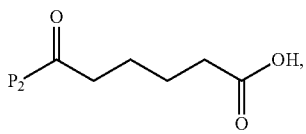

or a salt thereof, with a compound of formula (d):

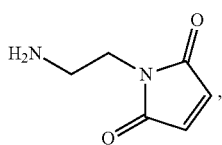
(d)

or a salt thereof, to form a compound of formula (VII):

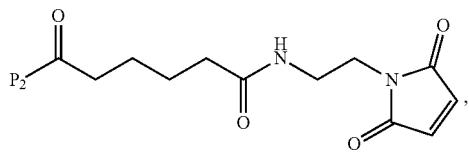
(VII)

or a salt thereof;

b) reacting the compound of formula (VII) or a salt thereof with a carboxylic acid deprotecting agent to form a compound of formula (VIIIa):

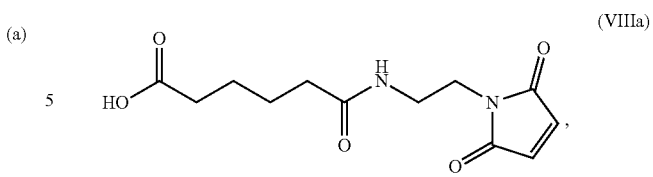
(VIIIa)

or a salt thereof;

c) reacting the compound of formula (VIIIa) or a salt thereof with a compound of formula (c-1):

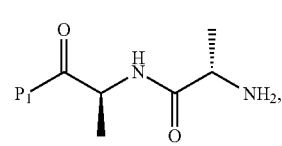
(c-1)

or a salt thereof, to form a compound of formula (IX-1):

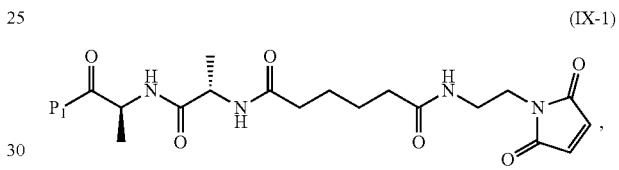
(IX-1)

or a salt thereof; and d) reacting the compound of formula (IX-1) or a salt thereof with a carboxylic acid deprotecting agent, wherein $P_1$ and $P_2$ are each independently a carboxylic acid protecting group.

In certain embodiments, for the method of the twenty-second embodiment, $P_1$ and $P_2$ are each independently a suitable carboxylic acid protecting group described herein. In certain embodiments, $P_1$ and $P_2$ are each independently —OMe, —O$^t$Bu, —OBn, —O-silyl (e.g., —OSi(Me)$_3$). In certain embodiments, $P_1$ and $P_2$ are both —O$^t$Bu.

To deprotect the carboxylic acid protecting group, any suitable carboxylic acid deprotecting agent known in the art can be used. Suitable deprotecting agents depend on the identity of the carboxylic acid protecting group. For example, when $P_1$ and $P_2$ are —O$^t$Bu, the protecting group can be removed by the treatment with an acid, a base or a suitable reductant. In certain embodiments, an acid can be used to remove the tert-butyl ester protecting group. Exemplary acids include, but are not limited to, formic acid, acetic acid, trifluoroacetic acid, hydrochloric acid, and phosphoric acid. In a specific embodiment, trifluoroacetic acid is used as the carboxylic acid deprotecting agent.

In certain embodiments, the deprotection reaction can be carried in any suitable organic solvent(s). Exemplary organic solvents include, but are not limited to, DMF, CH$_2$Cl$_2$, dichloroethane, THF, dimethylacetamide, methanol, ethanol, etc. In certain embodiments, the deprotection reaction is carried out in dichloromethane.

In certain embodiments, for the method of the twenty-second embodiment, the reaction between the compound of formula (VI) and the compound of formula (d) and the reaction between the compound of formula (VIIIa) and the compound of formula (c-1) are carried out in the presence of an activating agent. In certain embodiments, the activating agent is independently selected from a 2,4,6-trialkyl-1,3,5, 2,4,6-trioxatriphosphorinane 2,4,6-trioxide, carbodiimide, a uronium, an active ester, a phosphonium, 2-alkyl-1-alkyl-carbonyl-1,2-dihydroquinoline, 2-alkoxy-1-alkoxycarbonyl-1,2-dihydroquinoline, and alkylchloroformate. In certain embodiments, the activating agent is a 2,4,6-trialkyl-1,3,5,2,4,6-trioxatriphosphorinane 2,4,6-trioxide. In a specific embodiment, the activating agent is 2,4,6-tripropyl-1,3,5,2,4,6-trioxatriphosphorinane 2,4,6-trioxide.

Any suitable organic solvents can be used for the reaction between the compound of formula (VI) and the compound of formula (d) or between the compound of formula (VIIIa) and the compound of formula (c-1). In certain embodiments, the reaction is carried out in dichloromethane.

Compounds of the Invention

Also provided in the present invention is compounds described herein, e.g., compounds of formula (A), (dA), (A'), (dA'), (A-1), (dA-1), (II), (dII), (III), (dIII), (IV), (dIV), (IV-1), (dIV-1), (V), (dV), (V-1), (dV-1), (VI), (VI-1), (VII), (VIII), (VIIIa), (IX), (IX-1), (X), (X-1), (Xa), or (X-1a) or a salt thereof.

In certain embodiment, the compound of the present invention is represented by formula (VII), (VIII), (VIIIa), (IX-1), (X-1) or (X-1a) or a salt thereof.

In certain embodiments, the compounds described herein, such as compounds of formula (A), (A'), (A-1), (II), (III), (IV), (IV-1), (V), (V-1), (VI), (VI-1), (VII), (VIII), (VIIIa), (IX), (IX-1), (X), (X-1), (Xa), or (X-1a) or a salt thereof, are isotopically labeled or radio-labeled. Radio-labeled compounds of the compounds described herein could be useful in radio-imaging, in in vitro assays or in in vivo assays. "Isotopically labeled" or "radio-labeled" compounds are identical to compounds disclosed herein, but for the fact that one or more atoms are replaced or substituted by an atom having an atomic mass or mass number different from the atomic mass or mass number typically found in nature (i.e., naturally occurring). Any atom in the compounds of the disclosure not specifically labelled as an isotope is meant to represent the given element at about its natural isotopic abundance. For example, H represents protium ($^1$H) with a natural abundance of 99.985% and deuterium ($^2$H) with a natural abundance of 0.015%. Suitable radionuclides that may be incorporated in compounds include, but are not limited to, $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I, or $^{131}$I. In some embodiments, the radionuclide is $^3$H, $^{14}$C, $^{35}$S, $^{82}$Br or $^{125}$I. In some embodiments, the radionuclide is $^3$H or $^{125}$I. While the natural isotopic abundance may vary in a synthesized compound based on the reagents used, the concentration of naturally abundant stable hydrogen isotopes such as deuterium is negligible compared to the concentration of stable isotope in the compounds of Formulae (dA), (dA'), (dA-1), (dII), (dIII), (dIV), (dIV-1), (dV), and (dV-1). Thus, when a particular position of the compounds of Formulae (dA), (dA'), (dA-1), (dII), (dIII), (dIV), (dIV-1), (dV), and (dV-1), contains a deuterium atom, the concentration of deuterium at that position is substantially greater than the natural abundance of deuterium, which is 0.015%. In some embodiments, a position containing a deuterium atom has a deuterium enrichment or deuterium incorporation or deuterium concentration of at least 1%, of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%. The term "deuterium enrichment" refers to the percentage of incorporation of deuterium at a given position of the compounds of the disclosure in replacement of protium. Synthetic methods for incorporating radio-isotopes into organic compounds are applicable to compounds of the invention and are well known in the art. Examples of synthetic methods for the incorporation of tritium into target molecules are catalytic reduction with tritium gas, reduction with sodium borohydride or reduction with lithium aluminum hydride or tritium gas exposure labeling. Examples of synthetic methods for the incorporation of $^{125}$I into target molecules are Sandmeyer and like reactions, or aryl or heteroaryl bromide exchange with $^{125}$I.

All references cited herein and in the examples that follow are expressly incorporated by reference in their entireties.

EXAMPLES

The invention will now be illustrated by reference to non-limiting examples. Unless otherwise stated, all percentages, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument and LCMS were acquired on an Agilent 1260 Infinity LC with an Agilent 6120 single quadrupole MS using electrospray ionization (column: Agilent Poroshell 120 C18, 3.0×50 mm, 2.7 μm, 8 min method: flow rate 0.75 mL/min, solvent A: water with 0.1% formic acid, solvent B: MeCN, 5% to 98% of MeCN over 7 min and 98% MeCN for 1 min) and UPLC were acquired on a Waters, Acquity system with a single quadrupole MS Zspray™ (column: Acquity BEH C18, 2.1×50 mm, 1.7 μm, method: 2.5 min, flow rate 0.8 mL/min, solvent A: water, solvent B: MeCN, 5 to 95% of MeCN over 2.0 min and 95% MeCN for 0.5 min).

The following solvents, reagents, protecting groups, moieties and other designations may be referred to by their abbreviations in parenthesis:

Me=methyl; Et=ethyl; Pr=propyl; i-Pr=isopropyl; Bu=butyl; t-Bu=tert-butyl; Ph=phenyl, and Ac=acetyl
Ala=alanine
aq=aqueous
Bn=benzyl
DCM or CH$_2$Cl$_2$=dichloromethane
DIEA or DIPEA=N,N-diisopropylethylamine
DMA=N,N-dimethylacetamide
EEDQ=N-Ethoxycarbonyl-2-ethoxy-1,2-dihydroquinoline
EtOAc=ethylacetate
g=grams
h=hour
LC=liquid chromatography
LCMS=liquid chromatography mass spectrometry
min=minutes
mg=miligrams
mL=mililiters
mmol=milimoles
Me=methyl
MeOH=methanol
MS=mass spectrometry
MTBE=Methyl tert-butyl ether
NMR=nuclear magnetic resonance spectroscopy
RT or rt=room temperature (ambient, about 25° C.)
sat or sat'd=saturated T3P=2,4,6-trialkyl-1,3,5,2,4,6-trioxatriphosphorinane 2,4,6-trioxide
TFA=trifluoroacetic acid
THF=tetrahydrofuran
TLC=thin layer chromatography
UPLC=Ultra Performance Liquid Chromatography Example 1

Synthesis of (S)-tert-butyl 2-((S)-2-(6-((2-(2,5-dioxo-2,5-dihydro-1H-pyrrol-1-yl)ethyl)amino)-6-oxohexanamido)propanamido)propanoate (compound 1)

Step 1. Synthesis of tert-butyl 6-((2-(2,5-dihydro-2,5-dihydro-1H-pyrrol-1-yl)ethyl)amino)-6-oxohexanoate

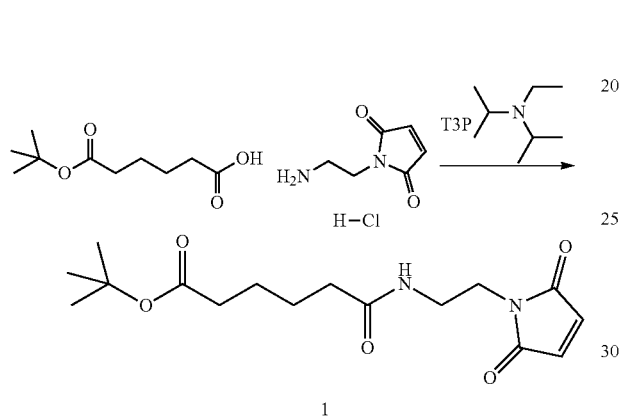

To a solution of 1-(2-aminoethyl)-1H-pyrrole-2,5-dione hydrochloride (0.288 g, 1.632 mmol) in dichloromethane (DCM) (5 ml, 17 vol) was added DIPEA (0.777 ml, 4.45 mmol), followed by 6-(tert-butoxy)-6-oxohexanoic acid (0.300 g, 1.483 mmol) as a solution in DCM (5 mL, 17 vol). Let reaction stir at RT and then charged 2,4,6-tripropyl-1,3,5,2,4,6-trioxatriphosphorinane 2,4,6-trioxide (T3P) (1.781 mL, 2.225 mmol) into the reaction. The reaction was stirred at RT until consumption of starting materials (2 h). The reaction was quenched with water (10 mL, 34 vol), layers separated and the aqueous layer was extracted once with DCM (10 mL, 34 vol). The combined organic layers were washed with sat'd NaHCO₃ (10 mL, 34 vol), brine (10 mL, 34 vol), dried over MgSO₄ and filtered. The filtrate was concentrated under vacuum and the resulting light brown oil was purified by silica gel chromatography (hexane to 100% EtOAc in 20 min,). Fractions containing product were combined and concentrated under vacuum and placed in vacuum to dry for 24 hours to obtain desired product, compound 1 (0.409 g, 88.5% yield) desired M/Z=324.38, found M+1=325.4. The proton NMR for compound 1 is shown in FIG. 1.

Step 2. Synthesis of 6-((2-(2,5-dioxo-2,5-dihydro-1H-pyrrol-1-yl)ethyl)amino)-6-oxohexanoic acid

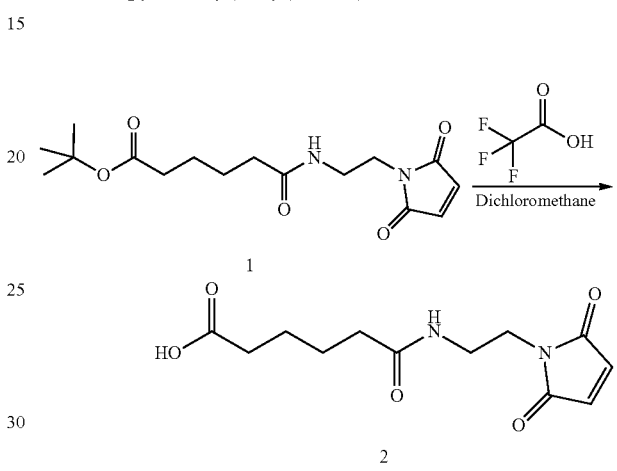

Figure 2:
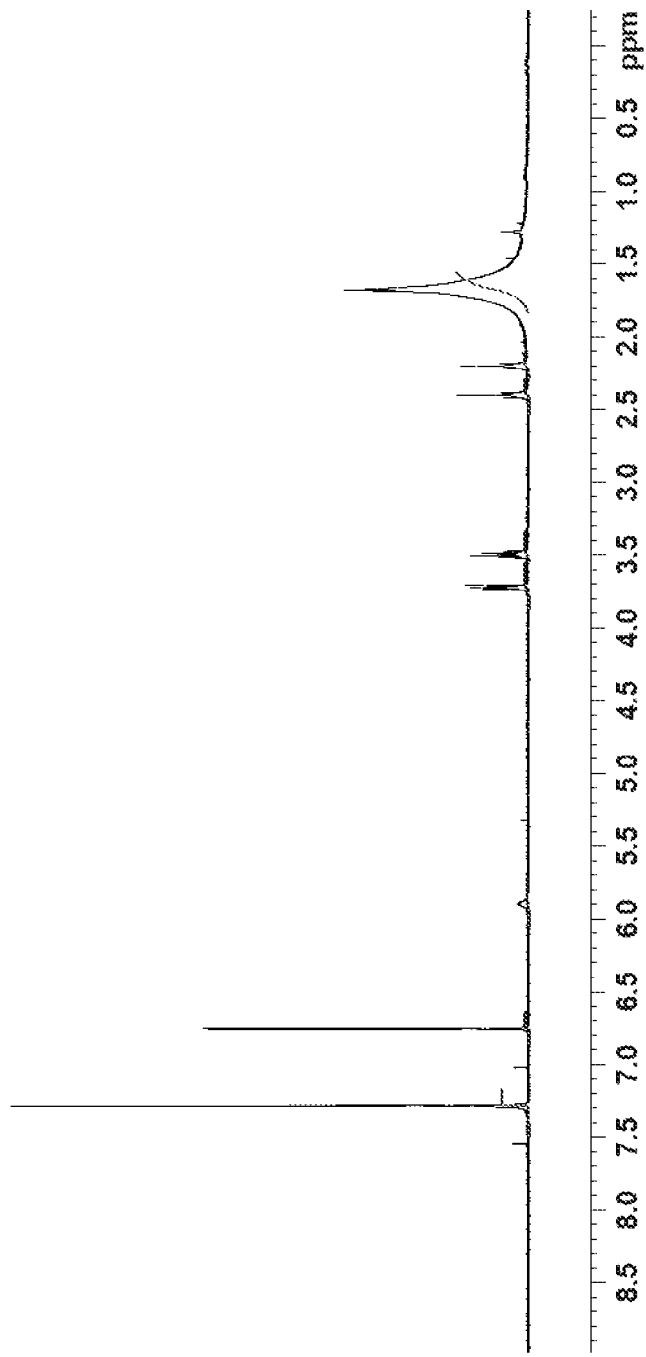

Compound 1 (0.400 g, 1.233 mmol), was dissolved in a mixture of DCM TFA (1/1 solution 8.0 mL, 20 vol) at RT and was stirred for 60 minutes. The reaction mixture was concentrated under vacuum, co-evaporated with toluene (2×5.0 mL, 2×12.5 vol) to obtain compound 2 as a white solid and was used without further purification (0.331 g, 100% yield). Proton NMR for compound 2 is shown in FIG. 2.

Step 3. Synthesis of (S)-tert-butyl 2-((S)-2-(6-((2-(2,5-dioxo-2,5-dihydro-1H-pyrrol-1-yl)ethyl)amino)-6-oxohexanamido)propanamido)propanoate

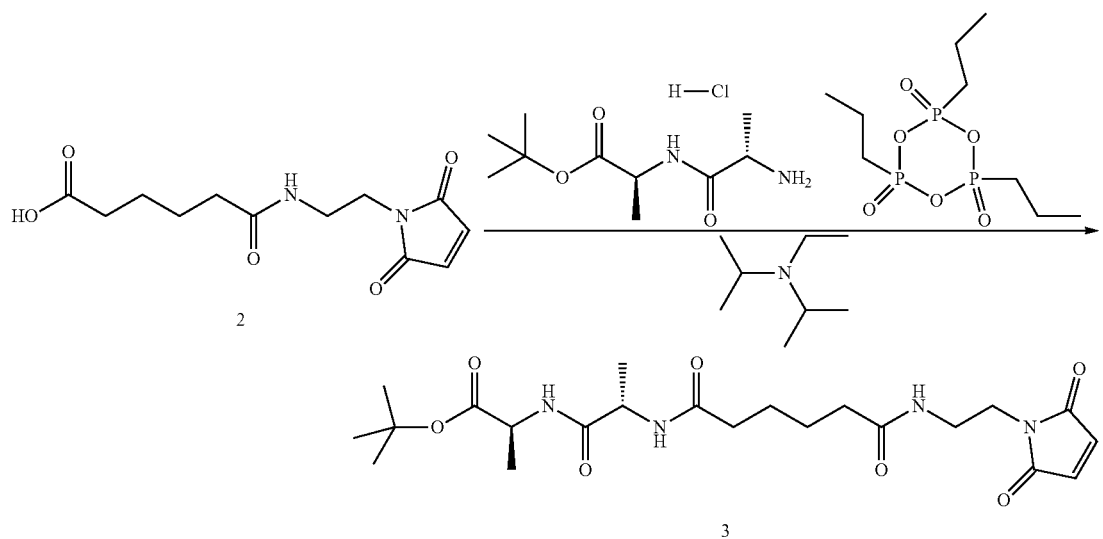

Compound 2 (0.331 g, 1.233 mmol) was dissolved in DCM (5.0 mL, 15 vol). The mixture was charged with DIPEA (0.3 mL) followed by T3P (1.233 ml, 1.603 mmol). A solution of tert-butyl L-alanyl-L-alaninate hydrochloride (312 mg, 1.233 mmol) in DIPEA (0.3 mL) was then added. The reaction was stirred at rt for 2 h before quenching with water (5.0 mL, 15 vol). The layers were separated and the aqueous layer was extracted once with DCM (5.0 mL, 15 vol). The combined organic layers were washed with sat'd NaHCO₃ (5.0 mL, 15 vol) and brine (5.0 mL, 15 vol), dried over MgSO₄, filtered and concentrated under vacuum to give desired product (compound 3) as a white/gel like product.

Figure 3:
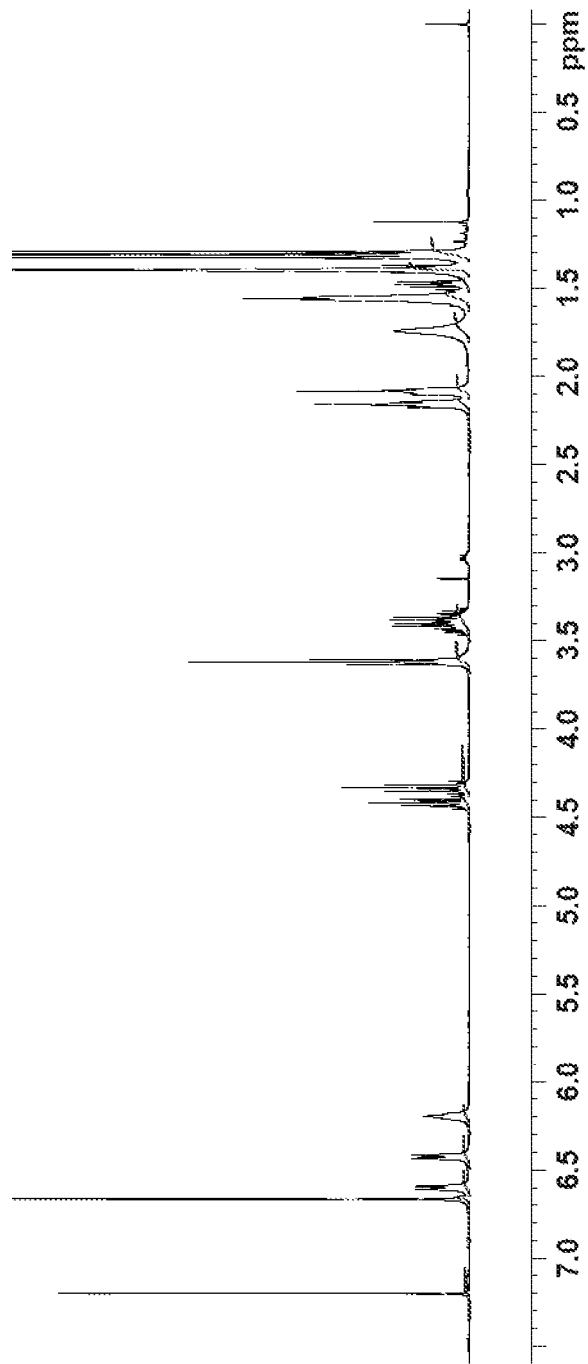

The crude product recrystallized by with hot DCM (3.5 mL, 10 vol), followed by dropwise addition of MTBE (1.0 mL, 3 vol). A white gel like product was formed and filtered to give desired product, compound 3. desired M/Z=466.24, found M+1=467.6. Proton NMR for compound 3 is shown in FIG. 3.

Step 4. Synthesis of (S)-2-((S)-2-(6-((2-(2,5-dioxo-2,5-dihydro-1H-pyrrol-1-yl)ethyl)amino)-6-oxo-hexanamido)propanamido)propanoic acid In a 250 mL round bottom flask equipped with magnetic stirring, J-Kem for temperature control, blanket nitrogen, and condenser was charged with (5-nitro-1,3-phenylene) dimethanol (5.0 g, 27.3 mmol). Toluene (90.0 mL, 18 vol) was added and the resulting suspension was stirred at room temperature. To the reaction was charged concentrated hydrochloric acid (37%, 10.0 mL, 2 vol) and the reaction was stirred at room temperature for 10 minutes. The reaction was then heated to 95° C. Upon heating to 45° C. the reaction became clear with light orange tinge. The reaction was heated at 95° C. overnight. After stirring at 95° C. overnight, the reaction was cooled to room temperature. The reaction was observed to be biphasic with small water layer at bottom (~5.0 mL). The reaction was transferred to a 250 mL separatory funnel and washed with water (2×50 mL, 2×10 vol) followed by saturated sodium bicarbonate (1×50 mL, 1×10 vol). The pH of the final wash was 6.0 determined by pH strip. The organic phase was retained and concentrated under vacuum to half the volume (~50 mL, 10 vol), resulting in slightly hazy solution. The solution was stirred in ice/water bath resulting in precipitation. The solution was allowed to crystallize at 2° C. for 3 hours. The white solid was filtered off under vacuum and was dried under vacuum at 40° C. to for 24 hours to obtain compound 5(3.67 g,

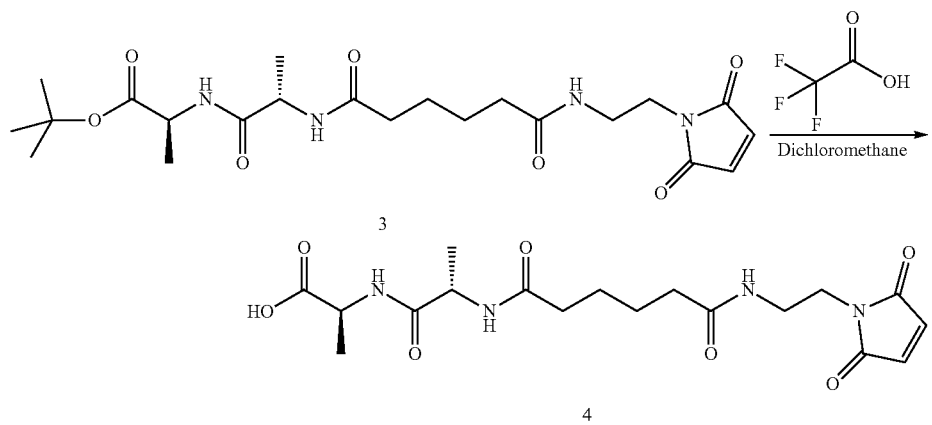

Compound 3, was dissolved in DCM (4 mL). TFA (2 mL) was added and the reaction was stirred at room temperature for 2 hours after which the reaction was concentrated under vacuum to give a clear yellow oil. The oil was co-evaporated with toluene (3×5.0 mL, 3×15 vol).

The oil was then triturated with hot DCM (3.5 mL, 10 vol) and MBTE (1.0 mL, 3 vol) was added to deliver a white/yellow solid as the desired product. Solid was dried under vacuum to yield compound 4 (0.350 g, 69.2% yield), desired M/Z=410.18, found M+1=411.5.

Example 2

Synthesis of (3-(chloromethyl)-5-nitrophenyl)methanol, compound 5

66.0% yield). Desired M/Z 201.02 found M−1+2Na 246.00. UPLC retention time: 1.38 min Example 3

Synthesis of (S)-9-((3-(chloromethyl)-5-nitrobenzyl)oxy)-8-methoxy-11,12,12a,13-tetrahydro-6H-benzo[5,6][1,4]diazepino[1,2-a]indol-6-one, compound 6

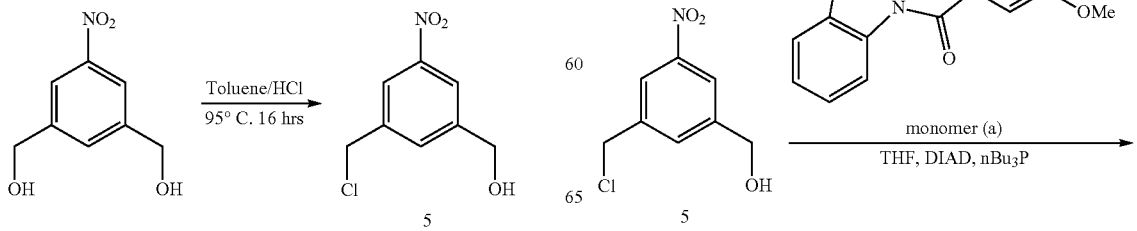

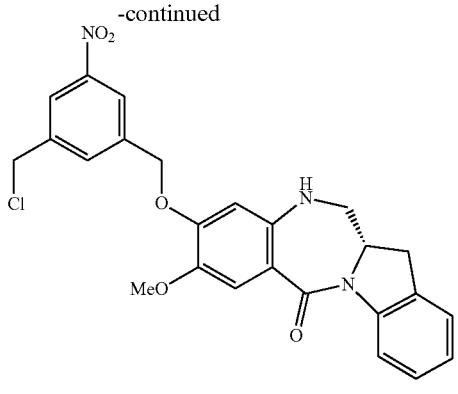

6

In a 250 mL round bottom flask equipped with J-Kem, magnetic stirring, nitrogen overlay, and cooling bath was charged monomer (a) (1.0 g, 3.375 mmol) and THF (20 mL, 20 vol) and the resulting solution was stirred at 19.5° C. (room temperature (RT)). The solution was slightly cloudy with some undissolved particulates. Compound 5 (0.82 g, 4.05 mmol) was added to the solution and the resulting mixture was stirred at RT. To the mixture was charged tri-n-butylphosphine (0.843 mL, 3.375 mmol) and cooled to 5° C. in ice water bath. The reaction was still cloudy. Diisopropyl azodicarboxylate, DIAD (0.664 mL, 3.375 mmol) was slowly dropped into reaction in a manner so that the exotherm is controlled. The reaction mixture turned clear orange in color (note if reaction turns dark orange/black the rate of addition is too fast). Upon full addition, the reaction turned light orange in color. The cooling was removed and the reaction was warmed to RT and was stirred overnight. Additional tri-n-butylphosphine (0.169 mL, 0.675 mmol) was added to the reaction and cooled to 5° C. in ice water bath at which point the reaction solution was still cloudy. DIAD (0.133 mL, 0.675 mmol) was added dropwise into the reaction in a manner so that the exotherm is controlled. Reaction turned clear orange in color (note if reaction turns dark orange/black the rate of addition is too fast). Upon full addition reaction turns light orange in color. Removed cooling and reaction was warmed to RT for 1 hour. The reaction mixture was concentrated under vacuum and then re-dissolved in dichloromethane (50 mL, 50 vol). The resulting dichloromethane solution was washed with water (2×25 mL, 2×25 vol). The organic phase was retained and slurried with potassium carbonate supported silica gel (1.0 g) to remove unreacted monomer (a). The silica gel was removed by filtration using Buchner funnel under vacuum and the resulting filtrate was concentrated to 5.0 mL (5 vol). The product was purified by silica gel chromatography (0-55% EtOAc/hexanes) to obtain compound 6 (1.0 g, 61.7% yield), Desired M/Z 479.12, found M+1 480.4. UPLC retention time: 1.88 min Example 4

Synthesis of (S)-8-methoxy-9-((3-((((S)-8-methoxy-6-oxo-11,12,12a,13-tetrahydro-6H-benzo[5,6][1,4]diazepino[1,2-a]indol-9-yl)oxy)methyl)-5-nitrobenzyl)oxy)-12a,13-dihydro-6H-benzo[5,6][1,4]diazepino[1,2-a]indol-6-one, Compound 7

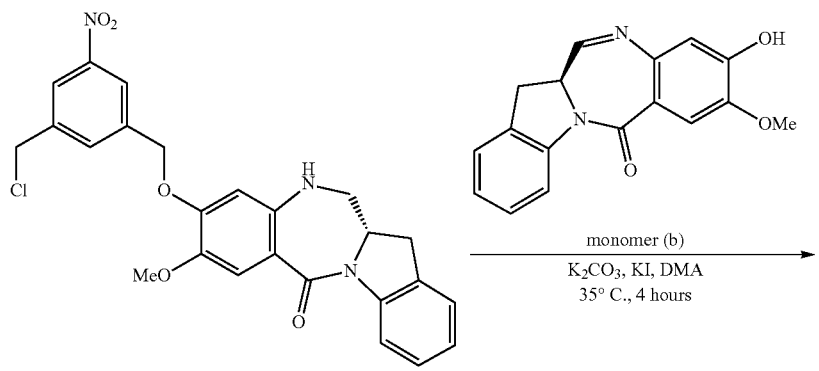

6

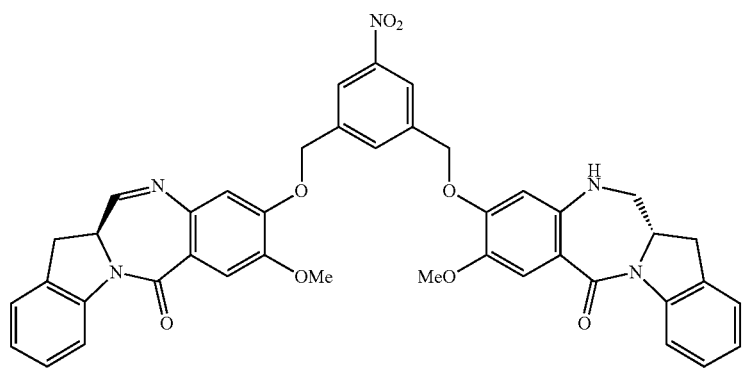

7

In a 250 mL flask equipped with J-Kem, magnetic stirring, nitrogen overlay, and heating mantle was charged compound 6 (1.0 g, 2.08 mmol). Dry DMA (20 mL, 20 vol) was added and the resulting mixture was stirred at RT resulting in a light brown solution. Monomer (b) (0.644 g, 2.19 mmol) was added and the resulting mixture was stirred at RT. KI (0.173 g, 1.04 mmol), was then added followed by K₂CO₃ (0.576 g, 4.17 mmol) and the resulting reaction mixture was stirred at RT and then heated at 35° C. for 4 hours. The reaction was cooled to room temperature and water (20 mL, 20 vol) was added to quench the reaction and precipitate the product. Upon water addition reaction is exothermic (20° C. to 40° C.). The resulting mixture was filtered and the solid was washed with water (50 mL, 50 vol). The solid was retained and dissolved in dichloromethane (40 mL, 40 vol) and transferred to a separatory funnel. The organic phase was washed with brine (2×20 mL, 2×20 vol) followed by water (2×20 mL, 2×20 vol). The organic phase was retained and concentrated to 10 mL (10 vol) and then slowly added into MTBE (40 mL, 40 vol) resulting in the formation of a light orange solid in solution. The solution was cooled in ice/water bath and stirred for 1 hour. The solid was filtered under vacuum dried under vacuum for 24 hours to yield compound 7 (1.6 g,). Desired M/Z 737.25, found M+1 738.6. UPLC retention time: 5.89 min Example 5

Compound 7 (2.38 g, 3.22 mmol) was dissolved in anhydrous THF (30 mL, 12 vol), anhydrous MeOH (4 mL) and water (2.0 mL). Ammonium chloride (1.82 g, 10 eq, 32.3 mmol) and iron powder (1.02 g, 16.1 mmol) were added. The mixture was stirred at 60° C. for 3 h while monitoring reaction for completion via UPLC.

The reaction mixture was cooled to rt, filtered through Celite and rinsed with DCM (60 mL, 25 vol). The resulting solution was concentrated to dryness on a rotary evaporator and then dissolved in DCM (50 mL, 20 vol) and transferred to a separatory funnel. Brine was added (50 mL, 20 vol), layers were separated and the organic layer was washed with water (2×25 mL, 2×10 vol). The organic layer was concentrated to dryness (deep orange syrup that foamed a little). The crude product was dissolved in DCM (10 mL, 4 vol) and was slowly dripped into stirring MTBE (50 mL, 20 vol). The resulting white slurry as cooled in ice water bath to 2.5° C. and stirred for 1 hour. After 1 hour the solid was filtered under vacuum and washed with MTBE (2×25 mL, 2×10 vol). The solid was dried under vacuum to obtain compound 8 (1.6 g, 70% yield, 80.66% purity by UPLC).

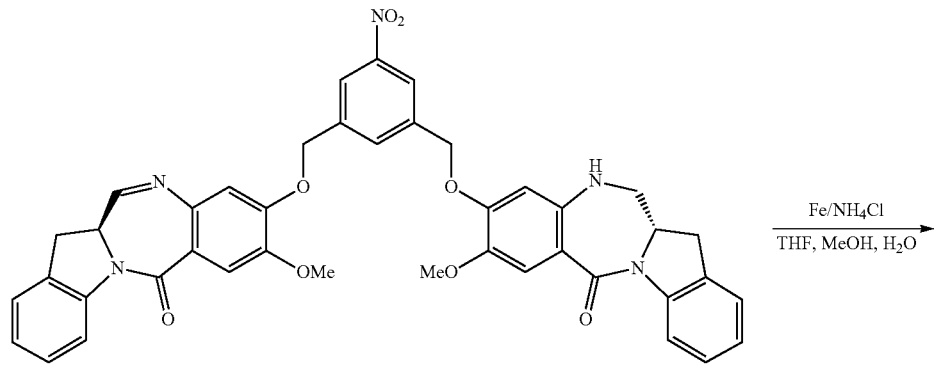

7

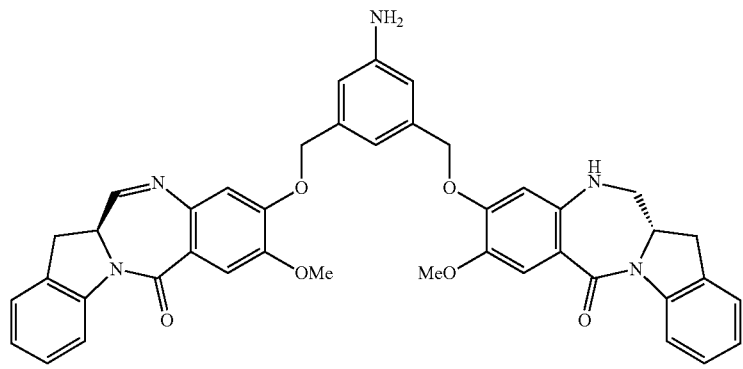

8

Example 6

Synthesis of N1-(2-(2,5-dioxo-2,5-dihydro-1H-pyrrol-1-yl)ethyl)-N6-((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)adipamide, compound 9

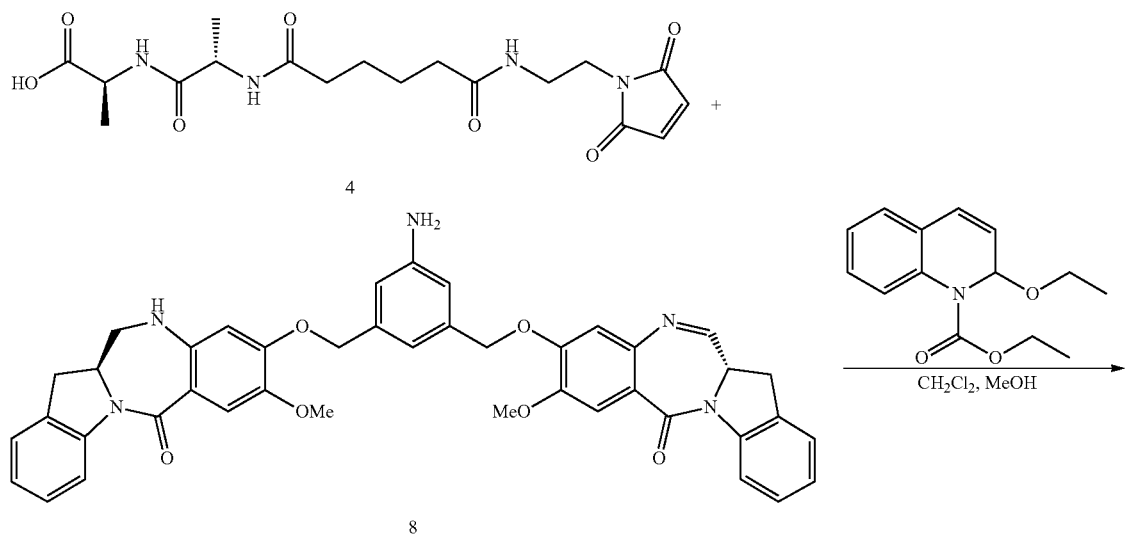

To a 50 mL round bottom flask was charged with compound 4 (0.0319 g, 0.078 mmol) followed by DCM (3.0 mL, 100 vol). EEDQ was then charged to the reaction and the resulting mixture was stirred for 5 min Methanol (0.20 mL, 10 vol) was charged to the reaction to produce a clear solution. To the reaction solution was charged with a solution of compound 8 (50 mg, 0.071 mmol) in DCM (1.0 mL, 30 vol) and the reaction was stirred at rt for 6 h.

After completion, the reaction was concentrated to 2.0 mL (63 vol). MTBE (4.0 mL, 125 vol) was added to the reaction and white precipitate was formed. The resulting suspension was stirred for 10 min at rt. The solid was filtered off to give a white yellow solid which was purified by silica gel chromatography (100% DCM to 90/10 DCM/MeOH) to yield compound 9 (0.037 g, 47.6% yield). UPLC retention time: 5.04 min Example 7

Synthesis of Deuterated Compound 8

Step 1: Reduction with borane-d₃-THF complex solution

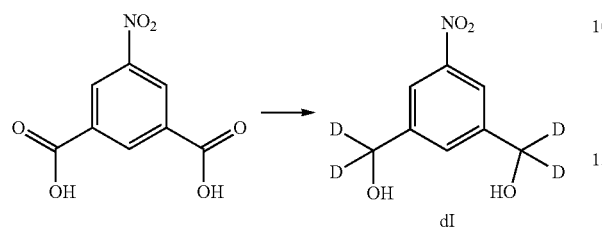

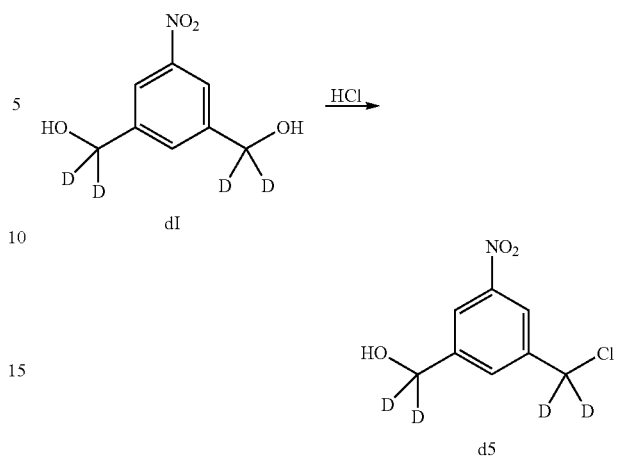

To a solution of 5-nitroisophthalic acid (0.8 g, 3.79 mmol) in tetrahydrofuran (8 ml) was added borane-d₃-THF complex solution (15.16 ml, 15.16 mmol) (1M solution, Aldrich, 97.5% D) dropwise at 0° C. The reaction slowly warmed to room temperature and was stirred 48 hours until consumption of the starting material was complete. After dropwise addition of Methanol (8 ml) the mixture was filtered and evaporated. The dry filtrate was dissolved in ethyl acetate and washed with saturated sodium bicarbonate, water, and brine. The organic was dried over magnesium sulfate, filtered and stripped to give compound dI (0.65 g, y=92%). The material was used crude without further purification. $^1$H NMR (400 MHz, DMSO-d$_6$) δ 5.46 (s, 1H), 7.70 (s, 1H), 8.04 (s, 2H)

Step 2: (5-nitro-1,3-phenylene)bis(methan-d2-ol) (0.176 g, 0.938 mmol) (compound dI) was suspended in toluene (3.13 ml). Concentrated hydrochloric acid (0.353 ml, 3.94 mmol) was added dropwise at ambient temperature. The reaction was then stirred at reflux (95° C.). After 18 hours the mixture was cooled to ambient temperature and transferred to separatory funnel with toluene and washed with water (1×15 mL) and aqueous sodium bicarbonate (1×15 mL). The organic layer was concentrated to dryness to get (3-(chloromethyl-d2)-5-nitrophenyl)methan-d2-ol (0.16 g, y=77% yield) (compound d5) as an off white solid. $^1$H NMR (400 MHz, DMSO-d$_6$) δ 5.54 (s, 1H), 7.85 (s, 1H), 8.15 (s, 1H), 8.20 (s, 1H). LCMS: 1.34 min on 2.5 min method.

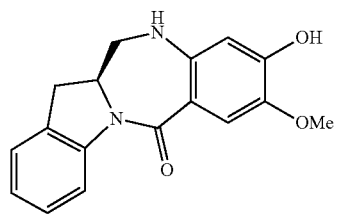

+

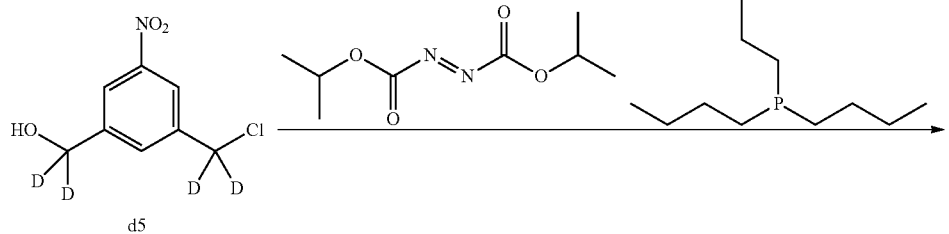

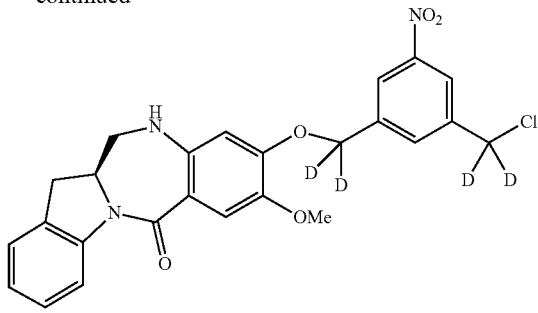

d6

Step 3: To a solution of (S)-9-hydroxy-8-methoxy-11,12,12a,13-tetrahydro-6H-benzo[5,6][1,4]diazepino[1,2-a]indol-6-one (140 mg, 0.472 mmol) and (3-(chloromethyl-d2)-5-nitrophenyl)methan-d2-ol (121 mg, 0.591 mmol) (compound d5) in anhydrous tetrahydrofuran (2953 μl) (stabilized with BHT) was added tri-n-butylphosphine (174 μl, 0.661 mmol) under nitrogen at room temperature. The mixture was cooled to 0° C. in an ice bath. After stirring 10 minutes diisopropyl (E)-diazene-1,2-dicarboxylate (139 μl, 0.661 mmol) was added dropwise. The mixture was stirred from 0° C. to room temp over 1 hour upon which deionized water (2 mL) was added and stirred for 30 min. The reaction mixture was concentrated to remove tetrahydrofuran, then diluted with dichloromethane and washed with water (2×15 mL). The organic layer was dried with anhydrous magnesium sulfate, filtered and concentrated.

The crude material was purified by silica gel chromatography (ethyl acetate/dichloromethane). Fractions containing desired product were combined and concentrated to give a yellow oil, which was recrystallized in ethyl acetate/tert-butylmethylether. The resulting solid was filtered and washed with tert-butylmethylether to obtain (S)-9-((3-(chloromethyl-d2)-5-nitrophenyl)methoxy-d2)-8-methoxy-11,12,12a,13-tetrahydro-6H-benzo[5,6][1,4]diazepino[1,2-a]indol-6-one (57 mg, y=40% yield) (compound d6). $^1$H NMR (400 MHz, DMSO-$d_6$) δ 2.90 (dd, J=4.2 Hz, 17 Hz, 1H), 3.28 (dd, J=9.6, 12.8 Hz, 1H), 3.48 (dd, J=10.2, 17 Hz, 1H), 3.57 (dd, J=6, 12.8 Hz, 1H), 3.72 (s, 3H), 4.37 (m, 1H), 6.37 (d, J=5.6 Hz, 1H), 6.43 (s, 1H), 7.02 (t, J=7.6 Hz, 1H), 7.19 (t, J=7.6 Hz, 1H), 7.25 (d, J=7.2 Hz, 1H), 7.31 (s, 1H), 7.99 (s, 1H), 8.21 (d, J=8.4 Hz, 1H), 8.32 (s, 2H)

LCMS: 1.84 min on 2.5 min method MS (m/z), found 484.4 (M+1)$^+$

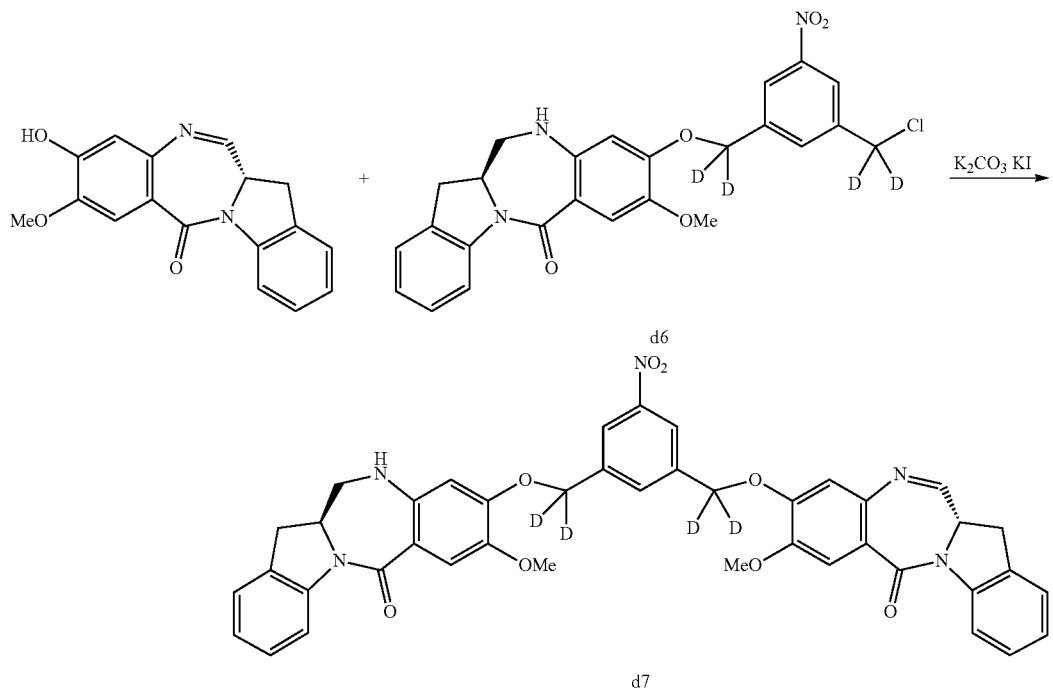

d7

Step 4: Potassium iodide (15.44 mg, 0.093 mmol) and anhydrous potassium carbonate (51.4 mg, 0.372 mmol) were added to a mixture of (S)-9-((3-(chloromethyl-d2)-5-nitrophenyl)methoxy-d2)-8-methoxy-11,12,12a,13-tetrahydro-6H-benzo[5,6][1,4]diazepino[1,2-a]indol-6-one (90 mg, 0.186 mmol) (compound d6) and (S)-9-hydroxy-8-methoxy-12a,13-dihydro-6H-benzo[5,6][1,4]diazepino[1,2-a]indol- 6-one monomer (57.5 mg, 0.195 mmol) in anhydrous DMA (1860 μl) under nitrogen at ambient temperature. After continuous stirring for 4.5 hours at 35 C the reaction mixture was diluted with water and the resulting solid was filtered. The solid was re-dissolved in dichloromethane, washed with water (1×10 mL), dried with anhydrous mag sulfate, filtered and concentrated. The crude material was re-dissolved in THF/ACN/DI water (3:2:1) and purified by RP-HPLC (Kromasil C18, Acetonitrile/Deionized water) Fractions containing desired product were extracted with dichloromethane. The organic extracts were concentrated in vacuo to obtain (S)-8-methoxy-9-((3-((((S)-8-methoxy-6-oxo-11,12,12a,13-tetrahydro-6H-benzo[5,6][1,4]diazepino[1,2-a]indol-9-yl)oxy)methyl-d2)-5-nitrophenyl)methoxy-d2)-12a,13-dihydro-6H-benzo[5,6][1,4]diazepino[1,2-a]indol-6-one (57 mg, y=41% yield) (compound d7). LCMS: 1.86 min on 2.5 min method MS (m/z), found 742.4 (M+1)$^+$ LCMS: 1.62 min on 2.5 min method MS (m/z), found 712.4 (M+1)$^+$ Alternatively, Compound of d7 can be Prepared as Follows:

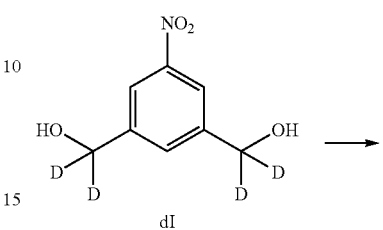

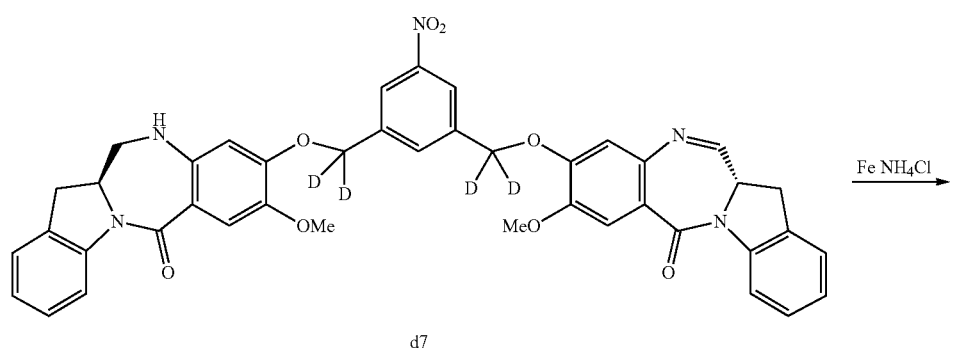

Step 5: (S)-8-methoxy-9-((3-((((S)-8-methoxy-6-oxo-11,12,12a,13-tetrahydro-6H-benzo[5,6][1,4]diazepino[1,2-a]indol-9-yl)oxy)methyl-d2)-5-nitrophenyl)methoxy-d2)-12a,13-dihydro-6H-benzo[5,6][1,4]diazepino[1,2-a]indol-6-one (57 mg, 0.077 mmol) (compound d7) was suspended in anhydrous tetrahydrofuran (1025 μl), anhydrous methanol (342 μl) and deionized water. Ammonium chloride (41.1 mg, 0.768 mmol) and iron (21.46 mg, 0.384 mmol) were added and the mixture was stirred for two hours at 65 C under nitrogen. The mixture was cooled to room temperature, diluted with 20% methanol/dichloromethane and filtered. The filtrate was concentrated filtrate and purified by silica gel chromatography (Methanol/Dichloromethane). Fractions containing desired product were combined and evaporated to obtain compound d8 (44 mg, y=80% yield) as a light yellow solid.

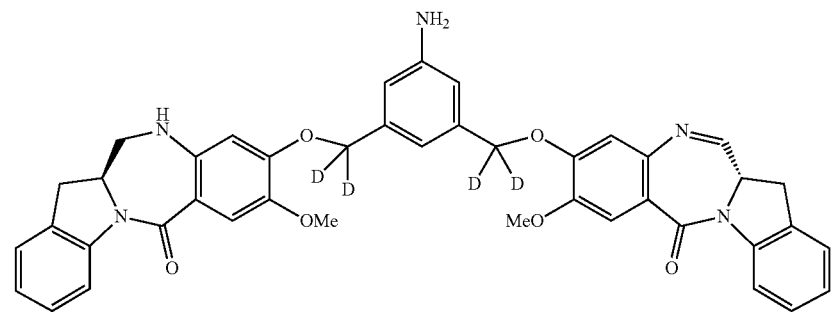

-continued

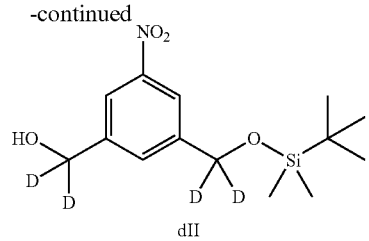

To a solution of compound dI (0.8 g, 4.27 mmol) in anhydrous dichloromethane (30 ml) at 0° C. was added N-ethyl-N-isopropylpropan-2-amine (1.509 ml, 8.55 mmol) followed by tert-butylchlorodimethylsilane (0.709 g, 4.70 mmol) as a solution in anhydrous N,N-dimethylformamide (5 ml). The reaction was stirred at 0° C. and monitored by TLC (dichloromethane/methanol: 9/1) to give a mixture of the starting material, mono and bis-protected products. After one hour the reaction was quenched with saturated ammonium chloride, and then the aqueous solution was extracted with dichloromethane (2×20 ml). The combined organic layers were washed with water (2×50 ml), brine, dried over magnesium sulfate, filtered and stripped to give a crude yellow oil. The material was then purified by silica gel chromatography in dichloromethane/methanol to isolate the desired product, compound dII (0.54 g, y=42%)

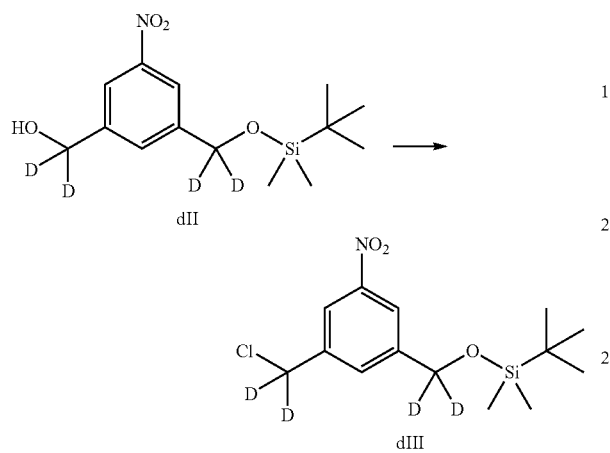

Compound dII (0.55 g, 1.825 mmol) was dissolved in anhydrous N,N-dimethylformamide (10 ml) and pyridine (0.515 ml, 6.39 mmol) was added. The reaction was cooled to 0° C., then methanesulfonyl chloride (0.282 ml, 3.65 mmol) was added dropwise, and reaction stirred for two hours, until completion of starting material. The mixture was first quenched with saturated sodium bicarbonate, then ethyl acetate was added and the layer separated. The aqueous layer was extracted with ethyl acetate (3×50 ml). The combined organic layers were washed with water, brine, dried over magnesium sulfate and filtered. The solvent was removed and the crude compound dIII (0.6 g, y=103%) was used in the next step without purification. UPLC=2.27 min (2.5 min method).

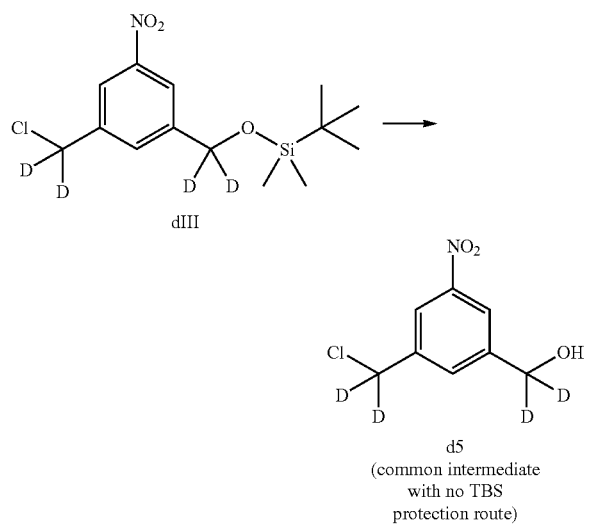

To a solution of compound dIII (0.6 g, 1.876 mmol) in anhydrous tetrahydrofuran (11.5 ml) was added N,N-Diisopropylethylamine (1.638 ml, 9.38 mmol) followed HF-pyridine (0.797 ml, 5.63 mmol) and the reaction was stirred at room temperature for two hours until completion of starting material. The reaction was quenched with saturated sodium bicarbonate then ethyl acetate was added and layers separated. The aqueous layer was extracted with ethyl acetate (3×10 ml) and the combined organic layers were washed with brine, dried over magnesium sulfate, filtered, and the solvent was removed in vacuo to give compound d5 that was carried on without purification (0.4 g, y=104%). UPLC=1.36 min (2.5 min method). $^1$H NMR (400 MHz, DMSO-$d_6$) δ 5.54 (s, 1H), 7.85 (s, 1H), 8.15 (s, 1H), 8.20 (s, 1H)

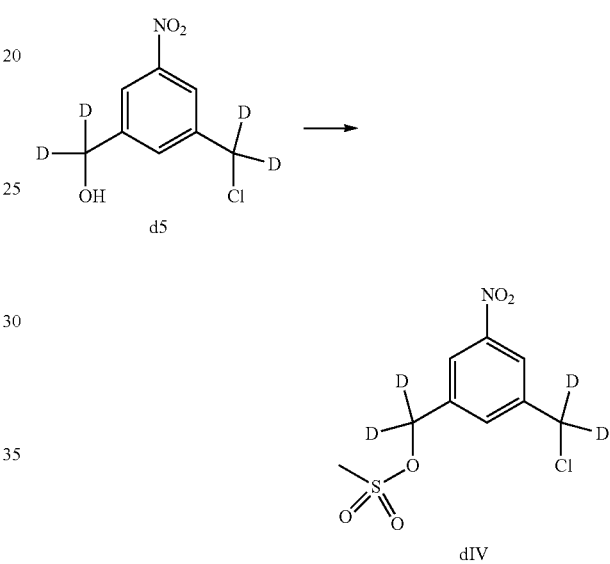

Compound d5 (400 mg, 1.945 mmol) was dissolved in anhydrous dichloromethane (12.5 ml) and cooled to 0° C. N,N-diisopropylethylamine (1019 μl, 5.84 mmol) was added followed by a solution of methanesulfonic anhydride (439 mg, 2.52 mmol) in dichloromethane. The reaction was stirred for approximately one hour until completion of the starting material. The reaction was quenched with cold water, the layers were separated and the aqueous layer was extracted with DCM (3×20 ml). The combined organic layers were washed with water, saturated sodium bicarbonate, brine, dried over magnesium sulfate and filtered. The excess of solvent was removed in vacuo and the crude material was used in the next step without further purification. UPLC=1.55 min (2.5 min method).

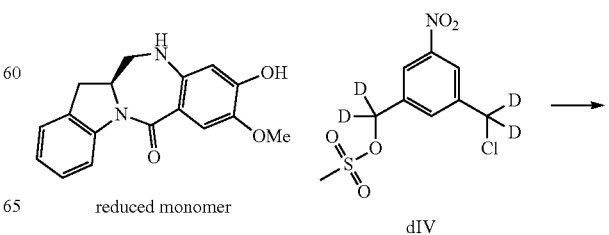

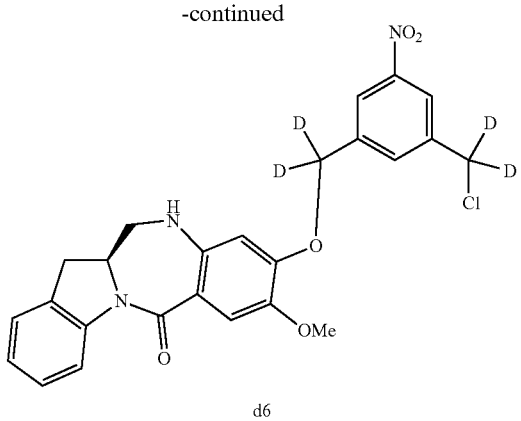

d6

To a solution of compound dIV (560 mg, 1.974 mmol) in anhydrous N,N-Dimethylacetamide (18.5 ml) was added potassium carbonate (818 mg, 5.92 mmol) followed by a solution of reduced monomer (614 mg, 2.072 mmol) in anhydrous N,N-Dimethylacetamide (15 ml). The reaction was stirred at room temperature for seven hours. Upon completion, the reaction was quenched with water and mixture stirred for ten minutes. The solid was filtered and then dissolved in dichloromethane/methanol (9/1) and washed with brine. The organic layer was separated and dried over magnesium sulfate, filtered and stripped. The crude material was purified by silica gel chromatography, using hexanes/ethyl acetate to give compound d6 (177 mg, y=18%). MS (m/z): 484.4 (M+1)$^+$. UPLC=1.86 min (2.5 min method).

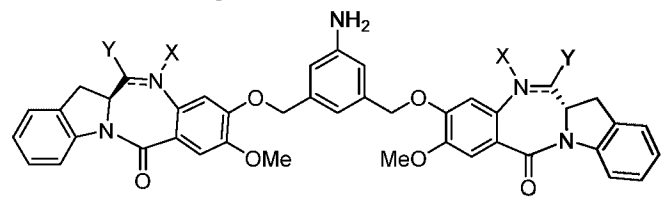

The invention claimed is:

1. A method of preparing a compound of formula (A):

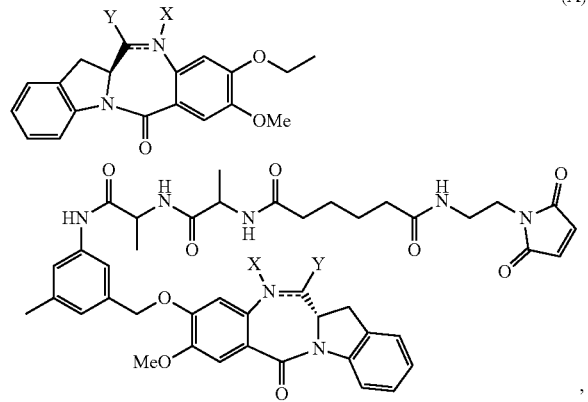

or a salt thereof, comprising reacting a compound of formula (V):

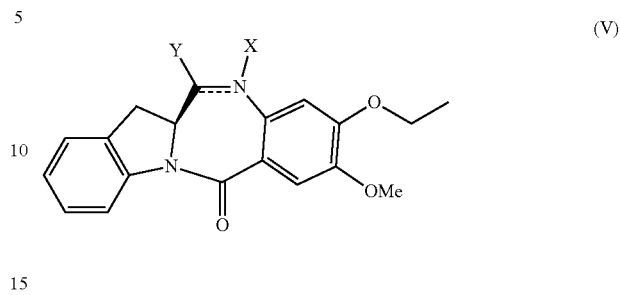

or a salt thereof, with a compound of formula (X):

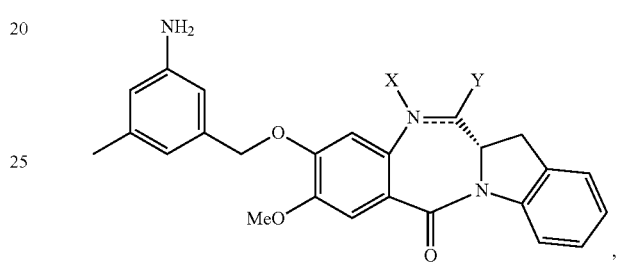

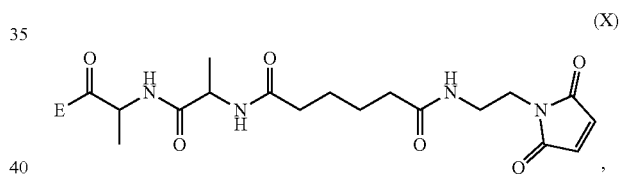

wherein:

each double line $==$ between N and C independently represents a single bond or a double bond, provided that when it is a double bond X is absent and Y is —H, and when it is a single bond, X and Y are both —H; and E is —OH, halide or —C(=O)E is an activated ester.

2. The method of claim 1, wherein the compound of formula (V) is prepared by reacting a compound of formula (IV):

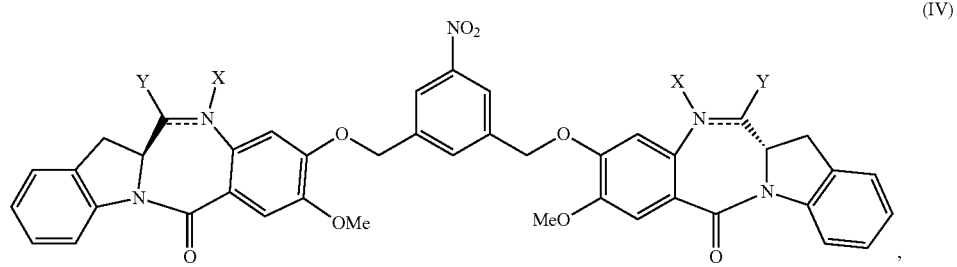

or a salt thereof, with a reducing agent to form the compound of formula (V):

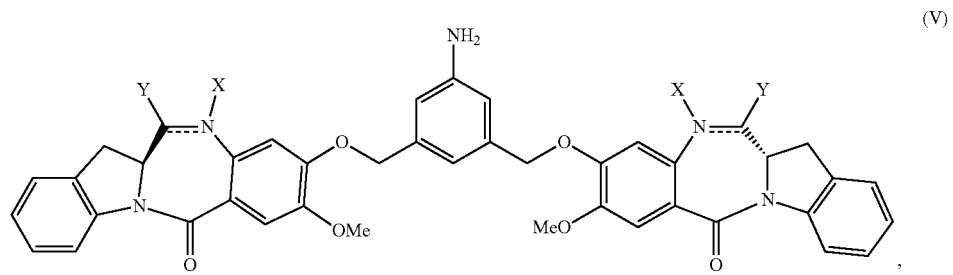

or a salt thereof.

3. A method of preparing a compound of formula (Xa):

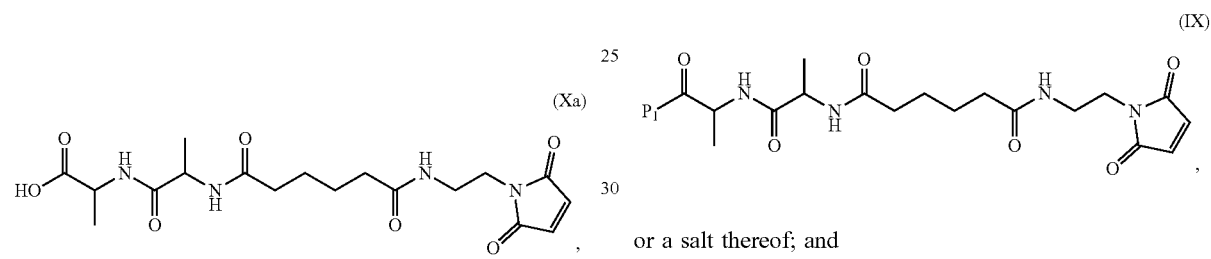

or a salt thereof, comprising the steps of:

1) reacting a compound of formula (VIII):

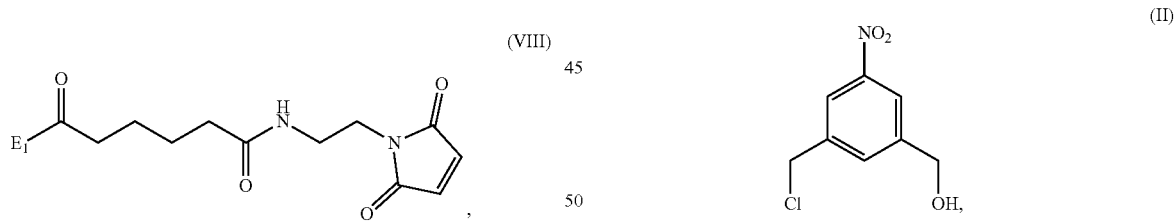

or a salt thereof, with a compound of formula (c):

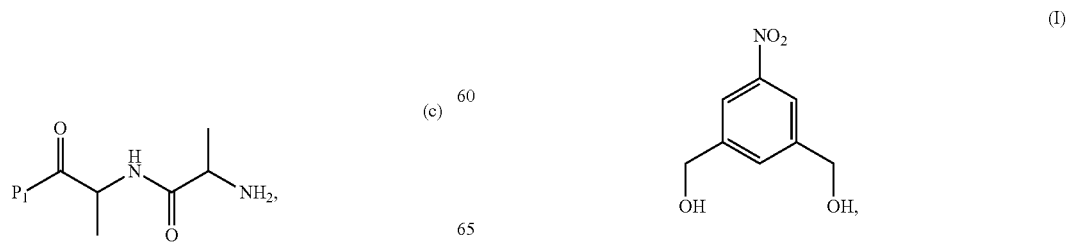

or a salt thereof, to form a compound of formula (IX):

(IX)

or a salt thereof; and 2) reacting the compound of formula (IX) with a carboxylic acid deprotecting agent to form the compound of formula (Xa) or a salt thereof, wherein $E_1$ is —OH, halide or —C(=O)$E_1$ is an activated ester; and $P_1$ is a carboxylic acid protecting group.

4. A method of preparing a compound of formula (II), (II)

comprising reacting a compound of formula (I):

(I)

with hydrochloric acid in toluene.

5. A method of preparing a compound of formula (IV-1):

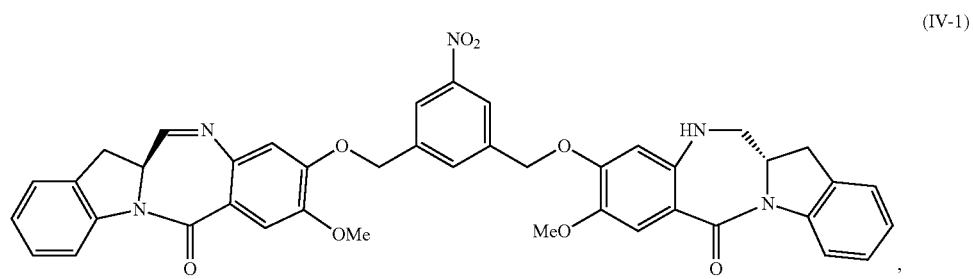 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

or a salt thereof, comprising the steps of:
1) reacting a compound of formula (I):

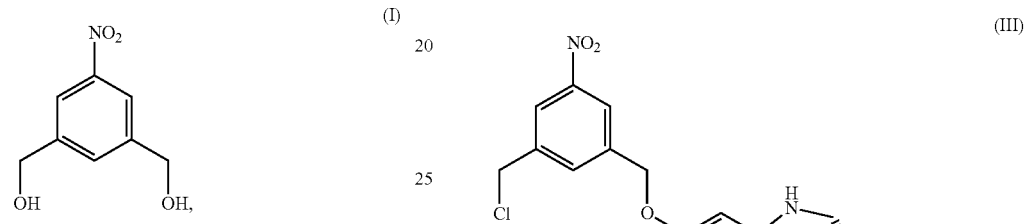

with hydrochloric acid in toluene to form a compound of formula (II):

2) reacting the compound of formula (II) with a monomer compound of formula (a),

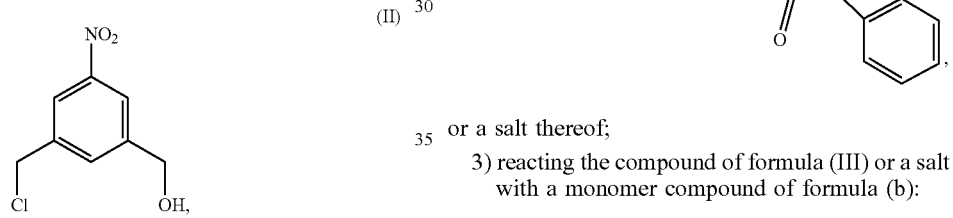

to form a compound of formula (III):

or a salt thereof;
3) reacting the compound of formula (III) or a salt thereof with a monomer compound of formula (b):

to form the compound of formula (IV-1) or a salt thereof.

6. A method of preparing a compound of formula (A-1)

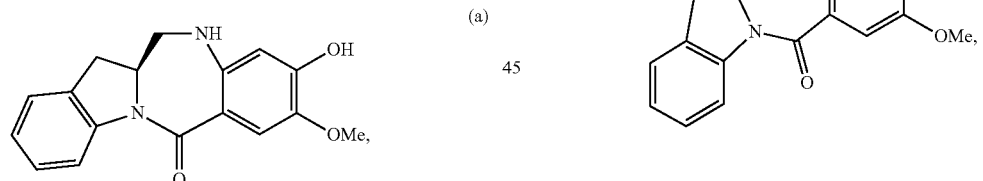

or salt thereof, comprising the steps of:
1) reacting a compound of formula (I):

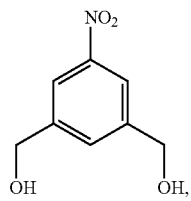

with hydrochloric acid in toluene to form a compound of formula (II):

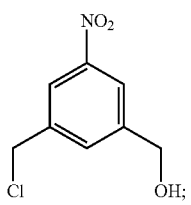

2) reacting the compound of formula (II) with a monomer compound of formula (a),

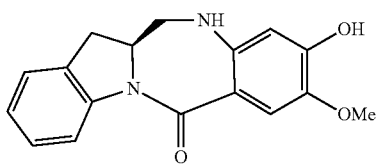

to form a compound of formula (III):

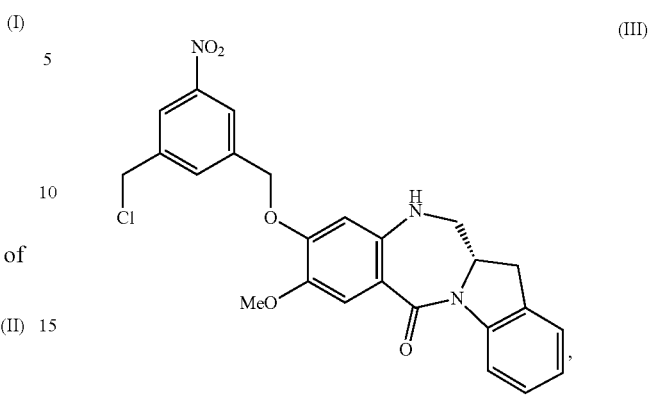

or a salt thereof;

3) reacting the compound of formula (III) or a salt thereof with a monomer compound of formula (b):

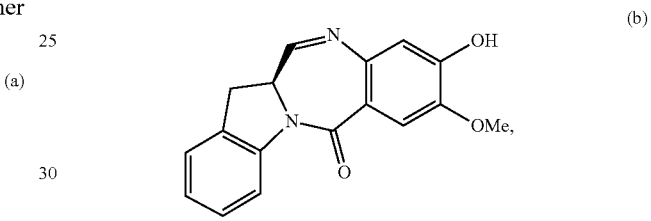

to form a compound of formula (IV-1):

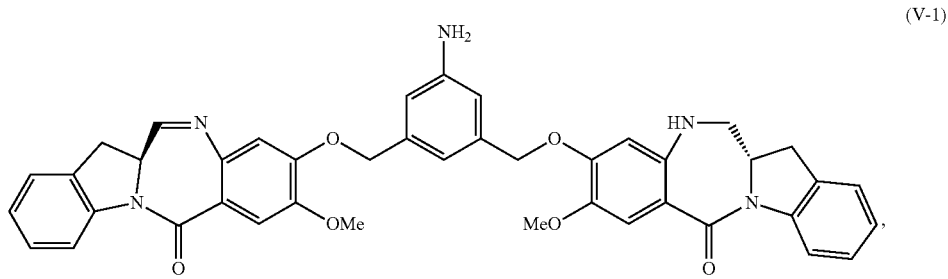 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

or a salt thereof;

4) reacting the compound of formula (IV-1) or a salt thereof with a reducing agent to form a compound of formula (V-1):

or a salt thereof; and 5) reacting the compound of formula (V-1) or a salt thereof, with a compound of formula (X-1):

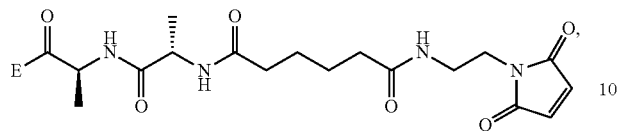
(X-1)

to form the compound of formula (A-1),
or a salt thereof, wherein E is —OH, halide or —C(=O)E is an activated ester.

7. The method of claim 5, wherein 30-38 w/w % of hydrochloric acid in water is reacted with the compound of formula (I).

8. The method of claim 7, wherein the reaction between the compound of formula (I) and hydrochloric acid is carried out at a temperature between 40° C. and 105° C., between 90° C. and 100° C. or the reaction is carried out at 95° C.

9. The method of claim 5, wherein the compound of formula (II) is purified by crystallization.

10. The method of claim 9, wherein the compound of formula (II) is crystalized in toluene.

11. The method of claim 5, wherein in step 2), the compound of formula (II) is reacted with the monomer compound of formula (a) in the presence of an alcohol activating agent.

12. The method of claim 11, wherein the alcohol activating agent is a trialkylphosphine, triarylphosphine, or triheteroarylphosphine.

13. The method of claim 12, wherein in step 2) the compound of formula (II) is reacted with the monomer compound of formula (a) in the presence of an azodicarboxylate.

14. The method of claim 13, wherein the alcohol activating agent is tributylphosphine and the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD).

15. The method of claim 13, wherein in step 3), the compound of formula (III) or a salt thereof is reacted with the monomer compound of formula (b) in the presence of a base.

16. The method of claim 15, wherein the base is sodium carbonate, potassium carbonate, cesium carbonate, sodium hydride, or potassium hydride.

17. The method of claim 15, wherein in step 3), the reaction between the compound of formula (III) or a salt thereof and the monomer compound of formula (b) is carried out in the presence of potassium iodide.

18. The method of claim 6, wherein in step 4), the reducing agent is Fe/NH$_4$Cl.

19. The method of claim 6, wherein the compound of formula (X-1) is represented by formula (X-1a):

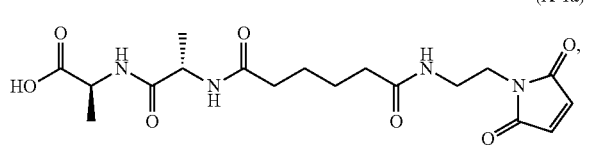
(X-1a)

and the compound of formula (X-1a) or a salt thereof is prepared by a method comprising the steps of:

a) reacting a compound of formula (VI):

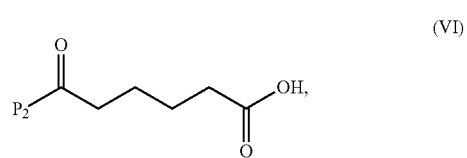
(VI)

or a salt thereof, with a compound of formula (d):

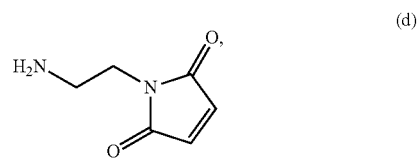
(d)

or a salt thereof, to form a compound of formula (VII):

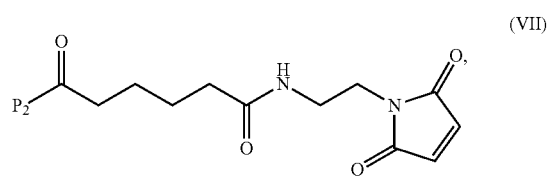
(VII)

or a salt thereof;

b) reacting the compound of formula (VII) or a salt thereof with a carboxylic acid deprotecting agent to form a compound of formula (VIIIa):

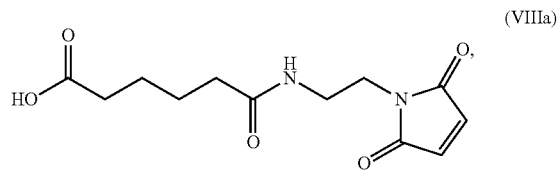 [SMILES: O=C(O)CCCCC(=O)NCCN1C(=O)C=CC1=O]
(VIIIa)

or a salt thereof;

c) reacting the compound of formula (VIIIa) or a salt thereof with a compound of formula (c-1):

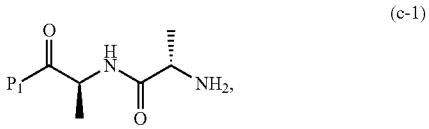
(c-1)

or a salt thereof, to form a compound of formula (IX-1):
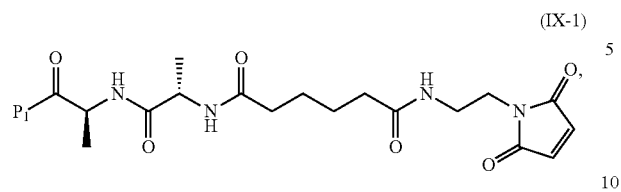
or a salt thereof; and
d) reacting the compound of formula (IX-1) or a salt thereof with a carboxylic acid deprotecting agent, wherein $P_1$ and $P_2$ are each independently a carboxylic acid protecting group.
* * * * *

UNITED STATES PATENT AND TRADEMARK OFFICE
CERTIFICATE OF CORRECTION

PATENT NO. : 10,385,071 B2  Page 1 of 2
APPLICATION NO. : 15/878991
DATED : August 20, 2019
INVENTOR(S) : Baudouin Gérard et al.

It is certified that error appears in the above-identified patent and that said Letters Patent is hereby corrected as shown below:

In the Claims

In Column 77, Lines 36-52 Claim 1 please replace the structure of formula (A) reproduced below:

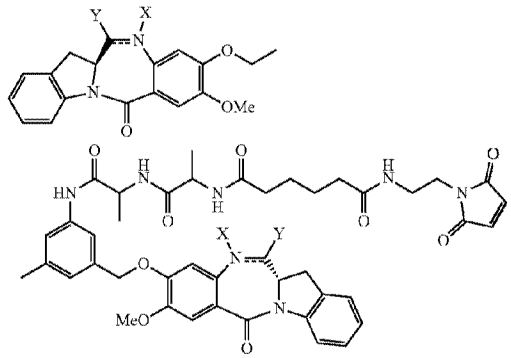

With the following structure:

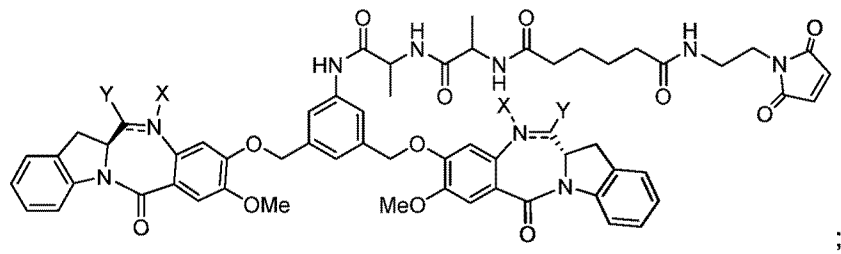

;

Signed and Sealed this
Seventeenth Day of December, 2019

Andrei Iancu
*Director of the United States Patent and Trademark Office*

CERTIFICATE OF CORRECTION (continued)
U.S. Pat. No. 10,385,071 B2

In Column 78, Lines 5-30 Claim 1 please replace the structure of formula (V) reproduced below:

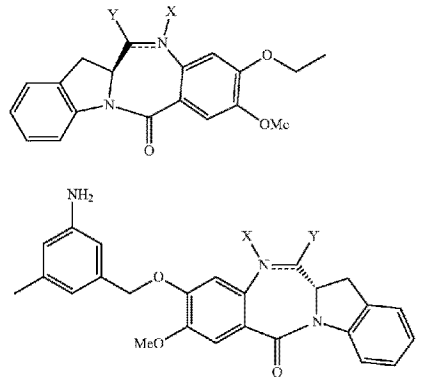

With the following structure: